US010603175B2

(12) United States Patent
Alambeigi et al.

(10) Patent No.: US 10,603,175 B2
(45) Date of Patent: Mar. 31, 2020

(54) CUTTING MACHINE FOR RESIZING RAW IMPLANTS DURING SURGERY

(71) Applicant: THE JOHNS HOPKINS UNIVERSITY, Baltimore, MD (US)

(72) Inventors: Farshid Alambeigi, Baltimore, MD (US); Shahriar Sefati, Baltimore, MD (US); Ryan Murphy, Baltimore, MD (US); Mehran Armand, Baltimore, MD (US); Chad R. Gordon, Baltimore, MD (US); Shuya Liu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 295 days.

(21) Appl. No.: 15/529,042

(22) PCT Filed: Nov. 24, 2015

(86) PCT No.: PCT/US2015/062516
§ 371 (c)(1),
(2) Date: May 23, 2017

(87) PCT Pub. No.: WO2016/086049
PCT Pub. Date: Jun. 2, 2016

(65) Prior Publication Data
US 2017/0252169 A1    Sep. 7, 2017

Related U.S. Application Data

(60) Provisional application No. 62/155,311, filed on Apr. 30, 2015.

(51) Int. Cl.
*A61F 2/30* (2006.01)
*B29C 64/188* (2017.01)
(Continued)

(52) U.S. Cl.
CPC .......... *A61F 2/30942* (2013.01); *A61B 34/10* (2016.02); *A61B 34/20* (2016.02);
(Continued)

(58) Field of Classification Search
None
See application file for complete search history.

(56) References Cited

U.S. PATENT DOCUMENTS 3,457,922 A    7/1969   Ray
4,436,684 A    3/1984   White
(Continued)

FOREIGN PATENT DOCUMENTS

WO    2012147114 A1    11/2012
WO    2013101753 A1    7/2013

OTHER PUBLICATIONS

Extended European Search Report dated Jul. 27, 2018 in corresponding EP Application No. 15862375, 8 pages.
(Continued)

*Primary Examiner* — Benjamin A Schiffman
(74) *Attorney, Agent, or Firm* — MH2 Technology Law Group, LLP

(57) ABSTRACT

Provided is a method for forming an implant with an autonomous manufacturing device. The method includes accessing a first computer-readable reconstruction of a being's anatomy; accessing a second computer-readable reconstruction of an implant; accessing a third computer-readable reconstruction comprising the first computer-readable reconstruction superimposed with the second computer readable reconstruction; generating at least one computer-readable trace from a point cloud; and forming an implant with an autonomous manufacturing device, wherein the
(Continued)

autonomous manufacturing device forms the implant into a shape defined by at least one dimension of the computer-readable trace.

22 Claims, 20 Drawing Sheets

(51) Int. Cl.
| | |
|---|---|
| *A61F 2/28* | (2006.01) |
| *A61B 34/10* | (2016.01) |
| *A61B 34/20* | (2016.01) |
| *B29C 64/386* | (2017.01) |
| *B23K 26/38* | (2014.01) |
| *B23K 103/14* | (2006.01) |
| *B23K 103/00* | (2006.01) |
| *A61B 34/30* | (2016.01) |
| *A61B 90/00* | (2016.01) |
| *B33Y 80/00* | (2015.01) |
| *B33Y 40/00* | (2020.01) |
| *B29L 31/00* | (2006.01) |
| *B33Y 10/00* | (2015.01) |

(52) U.S. Cl.
CPC ............ *A61F 2/2875* (2013.01); *B23K 26/38* (2013.01); *B29C 64/188* (2017.08); *B29C 64/386* (2017.08); *A61B 2034/102* (2016.02); *A61B 2034/105* (2016.02); *A61B 2034/108* (2016.02); *A61B 2034/2051* (2016.02); *A61B 2034/2055* (2016.02); *A61B 2034/304* (2016.02); *A61B 2090/3983* (2016.02); *A61B 2090/3991* (2016.02); *A61F 2002/3096* (2013.01); *A61F 2002/30952* (2013.01); *A61F 2002/30962* (2013.01); *B23K 2103/14* (2018.08); *B23K 2103/42* (2018.08); *B29L 2031/7532* (2013.01); *B33Y 10/00* (2014.12); *B33Y 40/00* (2014.12); *B33Y 80/00* (2014.12)

(56) References Cited

U.S. PATENT DOCUMENTS

| | | | |
|---|---|---|---|
| 5,279,575 | A | 1/1994 | Sugarbaker |
| 5,741,215 | A | 4/1998 | DUrso |
| 5,810,712 | A | 9/1998 | Dunn |
| 6,079,681 | A | 6/2000 | Stern et al. |
| 6,112,109 | A | 8/2000 | DUrso |
| 6,120,290 | A | 9/2000 | Fukushima et al. |
| 6,226,548 | B1 | 5/2001 | Foley et al. |
| 6,254,639 | B1 | 7/2001 | Peckitt |
| 6,285,902 | B1 | 9/2001 | Kienzle, III et al. |
| 6,491,699 | B1 | 12/2002 | Henderson et al. |
| 6,500,179 | B1 | 12/2002 | Masini |
| 6,608,628 | B1 | 8/2003 | Ross et al. |
| 6,726,678 | B1 | 4/2004 | Nelson et al. |
| 6,796,986 | B2 | 9/2004 | Duffner |
| 6,845,175 | B2 | 1/2005 | Kopelman et al. |
| 6,932,842 | B1 | 8/2005 | Litschko et al. |
| 7,050,877 | B2 | 5/2006 | Iseki et al. |
| 7,113,841 | B2 | 9/2006 | Abe et al. |
| 7,510,557 | B1 | 3/2009 | Bonutti |
| 7,596,399 | B2 | 9/2009 | Singhal et al. |
| 7,747,305 | B2 | 6/2010 | Dean et al. |
| 7,747,318 | B2 | 6/2010 | John et al. |
| 7,792,341 | B2 | 9/2010 | Schutyser |
| 7,857,821 | B2 | 12/2010 | Couture et al. |
| 7,953,260 | B2 | 5/2011 | Weinzweig et al. |
| 8,086,336 | B2 | 12/2011 | Christensen |
| 8,096,997 | B2 | 1/2012 | Plaskos et al. |
| 8,221,430 | B2 | 7/2012 | Park et al. |
| 8,221,461 | B2 | 7/2012 | Kuiper et al. |
| 8,357,165 | B2 | 1/2013 | Grant et al. |
| 8,397,732 | B2 | 3/2013 | Singhal et al. |
| 8,403,934 | B2 | 3/2013 | Angibaud et al. |
| 8,428,315 | B2 | 4/2013 | Suetens et al. |
| 8,518,085 | B2 | 8/2013 | Winslow et al. |
| 8,535,063 | B1 | 9/2013 | Amato |
| 8,650,005 | B2 | 2/2014 | Liao |
| 8,706,285 | B2 | 4/2014 | Narainasamy et al. |
| 8,781,557 | B2 | 7/2014 | Dean et al. |
| 9,208,558 | B2 | 12/2015 | Dean et al. |
| 9,216,084 | B2 | 12/2015 | Gordon et al. |
| 9,330,206 | B2 | 5/2016 | Dean et al. |
| 9,659,152 | B2 | 5/2017 | Mueller |
| 2001/0021851 | A1 | 9/2001 | Eberlein et al. |
| 2002/0035458 | A1 | 3/2002 | Kim et al. |
| 2002/0165552 | A1 | 11/2002 | Duffner |
| 2004/0091845 | A1 | 5/2004 | Azerad et al. |
| 2004/0172044 | A1 | 9/2004 | Grimm et al. |
| 2004/0204760 | A1 | 10/2004 | Fitz et al. |
| 2005/0043835 | A1 | 2/2005 | Christensen |
| 2005/0113846 | A1 | 5/2005 | Carson |
| 2005/0117696 | A1 | 6/2005 | Suzuki et al. |
| 2006/0142657 | A1 | 6/2006 | Quaid et al. |
| 2006/0195111 | A1 | 8/2006 | Couture |
| 2007/0167701 | A1 | 7/2007 | Sherman |
| 2007/0207441 | A1 | 9/2007 | Lauren |
| 2008/0304725 | A1 | 12/2008 | Lietner |
| 2008/0306490 | A1 | 12/2008 | Lakin et al. |
| 2008/0319448 | A1 | 12/2008 | Lavallee et al. |
| 2009/0088674 | A1 | 4/2009 | Caillouette et al. |
| 2009/0092948 | A1 | 4/2009 | Gantes |
| 2009/0099570 | A1 | 4/2009 | Paradis et al. |
| 2009/0220122 | A1 | 9/2009 | Richards et al. |
| 2009/0240141 | A1 | 9/2009 | Neubauer et al. |
| 2009/0281623 | A1 | 11/2009 | Kast et al. |
| 2009/0311647 | A1 | 12/2009 | Fang et al. |
| 2010/0145425 | A1 | 6/2010 | Jung et al. |
| 2010/0145898 | A1 | 6/2010 | Malfliet et al. |
| 2010/0261998 | A1 | 10/2010 | Stiehl |
| 2010/0311028 | A1 | 12/2010 | Bell et al. |
| 2011/0029093 | A1 | 2/2011 | Bojarski et al. |
| 2011/0066072 | A1 | 3/2011 | Kawoos et al. |
| 2011/0087465 | A1 | 4/2011 | Mahfouz |
| 2011/0102549 | A1 | 5/2011 | Takahashi |
| 2011/0117530 | A1 | 5/2011 | Albocher et al. |
| 2011/0196377 | A1 | 8/2011 | Hodorek et al. |
| 2011/0208256 | A1 | 8/2011 | Zuhars |
| 2011/0244415 | A1 | 10/2011 | Batesole |
| 2012/0041318 | A1 | 2/2012 | Taylor |
| 2012/0063655 | A1 | 3/2012 | Dean et al. |
| 2012/0109228 | A1 | 5/2012 | Boyer et al. |
| 2012/0259592 | A1 | 10/2012 | Liao |
| 2013/0035690 | A1 | 2/2013 | Mittelstadt et al. |
| 2013/0122463 | A1 | 5/2013 | Csillag |
| 2013/0204600 | A1 | 8/2013 | Mehra |
| 2013/0211424 | A1 | 8/2013 | Thiran et al. |
| 2013/0296872 | A1 | 11/2013 | Davison et al. |
| 2013/0297265 | A1 | 11/2013 | Baloch et al. |
| 2013/0310963 | A1 | 11/2013 | Davison |
| 2014/0045167 | A1 | 2/2014 | Anderson et al. |
| 2014/0122382 | A1 | 5/2014 | Elster et al. |
| 2014/0329194 | A1 | 11/2014 | Sachdeva et al. |
| 2014/0343557 | A1 | 11/2014 | Mueller |
| 2015/0272691 | A1 | 10/2015 | Kim et al. |
| 2015/0297309 | A1 | 10/2015 | Bly et al. |
| 2015/0328004 | A1 | 11/2015 | Mafhouz |
| 2016/0038243 | A1 | 2/2016 | Miller et al. |
| 2016/0045317 | A1 | 2/2016 | Lang et al. |
| 2016/0346091 | A1 | 12/2016 | Bin Abdul Rahman et al. |
| 2017/0014169 | A1 | 1/2017 | Dean et al. |
| 2017/0108930 | A1 | 4/2017 | Banerjee et al. |
| 2017/0273797 | A1 | 9/2017 | Gordon et al. |

OTHER PUBLICATIONS

International Search Report and Written Opinion in International Application No. PCT/US2015/062516, 10 pages.
Murphy et al., "Computer-assisted, Le Fort-based, face-jaw-teeth transplantation: a pilot study on system feasibility and translational

(56) References Cited

OTHER PUBLICATIONS assessment", International Journal of Computer Assisted Radiology and Surgery, Aug. 2014, pp. 1-10.
Lee, M. et al., "Custom implant design for patients with cranial defects", Engineering in Medicine and Biology Magazine, IEEE, 2002, vol. 21, pp. 38-44.
Goh, R. et al., "Customized fabricated implants after previous failed cranioplasty", Journal of Plastic, Reconstructive and Aesthetic Surgery, vol. 63, 2010, pp. 1479-1484.
Bell, R. B., "Computer Planning and Intraoperative Navigation in Orthognathic Surgery"; Journal of Oral and Maxillofacial Surgery; 2011, vol. 69, No. 3, pp. 592-605.
Cevidances, L. et al. Three-dimensional surgical simulation:, American Journal of Orhodontics and Dentofacial Orhopedics, vol. 138, Issue 3, Sep. 2010, pp. 361-371 (Year:2010).
Chapuis et al., "A new approach for 3D computer-assisted orthognathic surgery-first clinical case", Elsevier, International Congress Serier, vol. 1281, May 2005, pp. 1217-1222 (Year: 2005).
Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).
Extended European Search Report dated May 24, 2018 in corresponding EP Application No. 15862868, 8 pages.
Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.
Internatinal Search Report and Written Opinion in International Application No. PCT/US2015/062521, 12 pages.
International Search Report and Written Opinion dated Mar. 9, 2015 from corresponding International Application No. PCT/US2014/067671; 13 pages.
International Search Report and Written Opinion dated Sep. 12, 2016 for PCT/US2016/030447.
International Search Report dated Feb. 24, 2015 from corresponding International Application No. PCT/US2014/067504; 5 pgs.
International Search Report dated Mar. 13, 2015 from corresponding International Application No. PCT/US2014/067167; 5 pgs.
International Search Report dated Mar. 20, 2015 from corresponding International Application No. PCT/US2014/067692; 4 pgs.
International Search Report dated Mar. 5, 2015 from corresponding International Application No. PCT/US2014/067174; 4 pgs.
International Search Report dated Mar. 5, 2015 from corresponding International Application No. PCT/US2014/067656; 5 pgs.
International Search Reported dated Feb. 24, 2015 from corresponding International Application No. PCT/US2014/067504; 11 pgs.
International Search Reported dated Feb. 27, 2015 from corresponding International Application No. PCT/US2014/067581; 4 pgs.
Jalbert et al., "One-step primary reconstruction for complex craniofocial re section with PEEK custom-made implants", Jounal of Cranio-Maxillo-Facial Surgery, Mar. 2014, vol. 42, No. 2, pp. 141-148.
Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.
Murphy et al., "Computer-assisted single-stage cranioplasty", In: Engineering in Medicine and Biology Sociaty (EMBC), Aug. 25-29, 2015, pp. 4910-4912.
Schramm et al.; "Non-invasive Registration in Computer Assisted Craniomaxillofacial Surgery"; Rechner-und Sensorgestutzte Chirurgie, 2001, pp. 258-268.
Examination Report in Australian Corresponding Application No. 2015353601 dated Jul. 29, 2019, 4 pages.

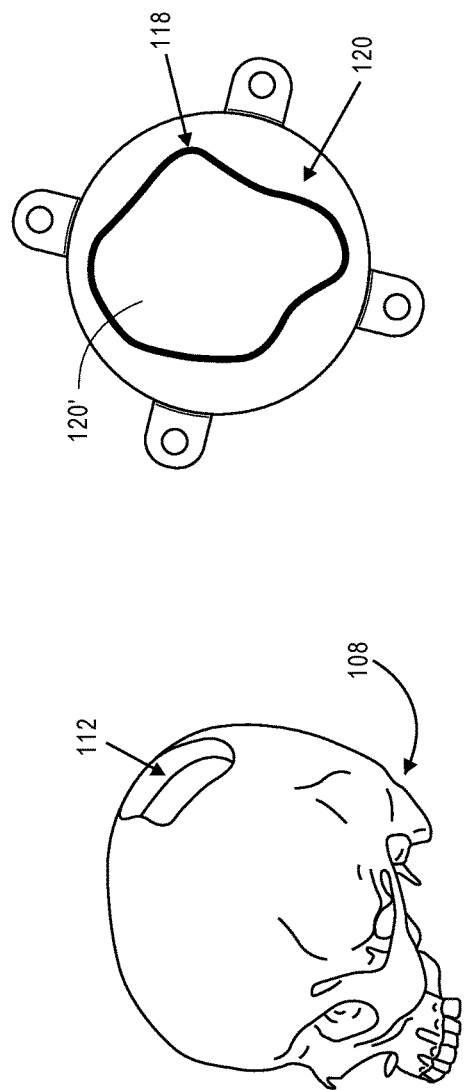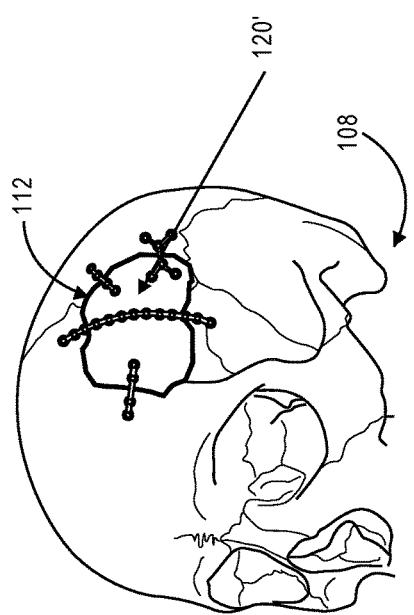
FIG. 7B
FIG. 7C
FIG. 7A

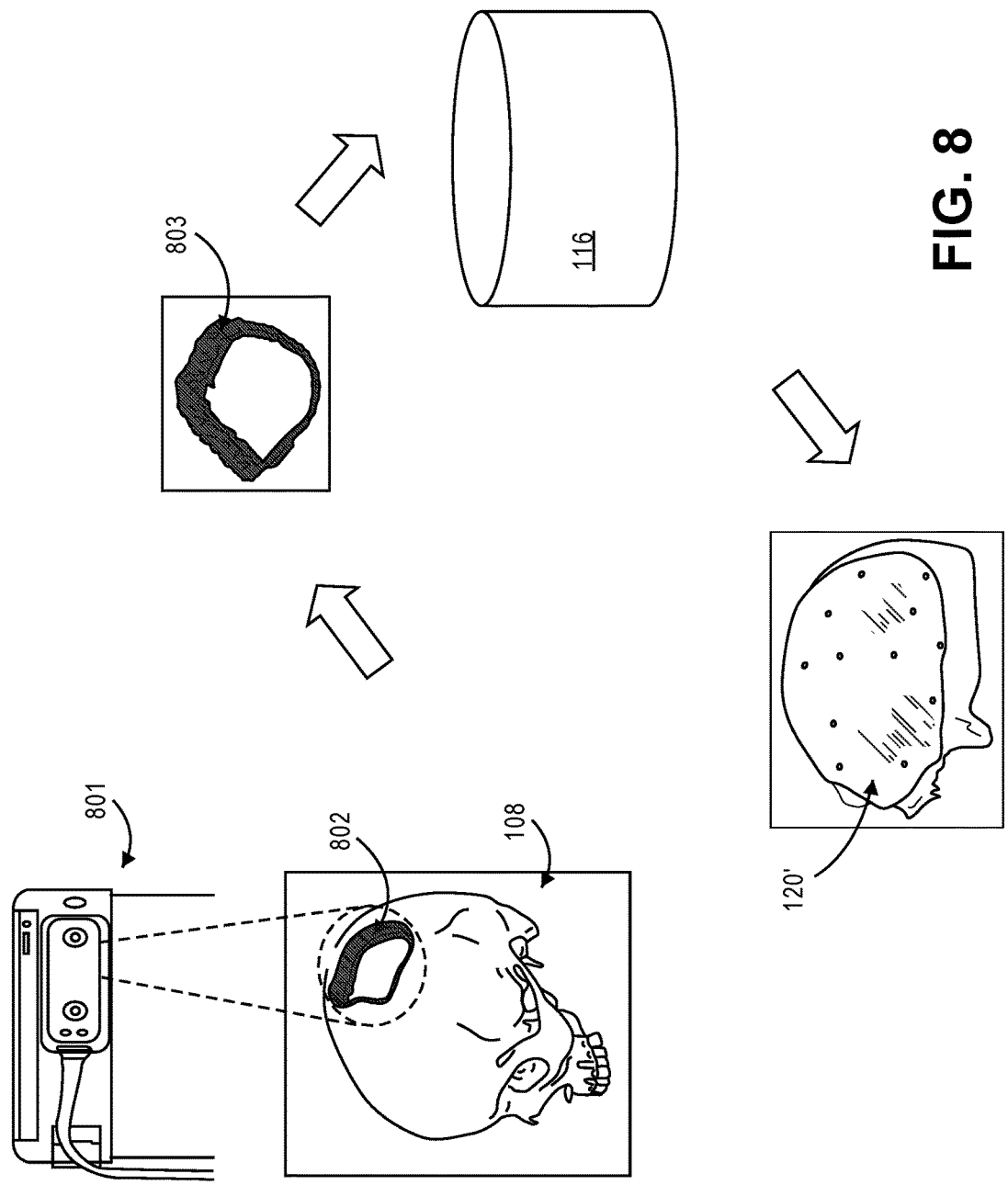

CUTTING MACHINE FOR RESIZING RAW IMPLANTS DURING SURGERY

CROSS-REFERENCE TO RELATED APPLICATIONS

This application is a U.S. National Stage application of PCT/US2015/062521 filed Nov. 24, 2015, which claims priority to U.S. Provisional Patent Application Ser. No. 62/155,311 entitled "A Cutting Machine For Resizing Raw Implants During Surgery" filed on Apr. 30, 2015, the entirety of which is incorporated herein by reference, and to Patent Cooperation Treaty Application Ser. Nos. PCT/US14/67167 entitled "Cranial Reference Mount" filed on Nov. 24, 2014, PCT/US14/67174 entitled "Patient-Specific Trackable Cutting Guides" filed on Nov. 24, 2014, PCT/US14/67504 entitled "Computer-Assisted Face-Jaw-Teeth Transplantation" filed on Nov. 25, 2014, PCT/US14/67656 entitled "Computer-Assisted Craniomaxillofacial Surgery" filed on Nov. 26, 2014, PCT/US14/67671 entitled "Computer-Assisted Planning and Execution System" filed on Nov. 26, 2014, PCT/US14/67581 entitled "Orthognathic Biomechanical Simulation" filed on Nov. 26, 2014, and PCT/US14/67692 entitled "Real-Time Cephalometry For Craniomaxillofacial Surgery" filed on Nov. 26, 2014, the entireties of which are incorporated herein by reference.

FIELD OF THE INVENTION

This invention relates generally to the field of surgery, particularly cranioplasty and craniomaxillofacial surgery, and specifically to the field of computer-assisted surgery, although it is not limited to these fields.

BACKGROUND OF THE INVENTION

Craniectomies requiring cranioplasty are either decompressive following stroke/trauma or occur as a result of oncological ablation for masses involving the bony calvarium. In the setting of trauma with cerebral edema, stroke with bleeding, or autologous bone flap osteomyelitic infections requiring removal, delayed cranioplasties are necessary at a secondary stage. In fact, nearly 250,000 primary brain tumors/skull-based neoplasms are diagnosed each year resulting in a range of 4500-5000 second-stage implant cranioplasties/year.

Craniectomy defects following resection of calvarial lesions are most often reconstructed using on-table manufacturing, similar to all defects in the craniomaxillofacial skeleton. For tumor ablative surgery—where tumors and/or processes involve the bony calvarium—cranioplasties are most often performed primarily using suboptimal hand-molding techniques. Currently, the standard of care is to reconstruct the cranial defects with on-table manipulation using a varying combination of materials. For example, oncological defects are commonly reconstructed with "off-the-shelf" materials, as opposed to using a pre-fabricated customized implant simply because the exact defect size/shape is unknown. As a result, a variety of materials may be used to reconstruct large cranial defects, including titanium mesh, porous hydroxyapatite (HA), polymethylmethacrylate (PMMA), and polyether ether ketone (PEEK), among others.

Some of these materials can be molded and/or shaped in the operating room to approximate complex, three-dimensional defects, especially in instances greater than 5 cm squared in size. Of note, the most frequently used material next to titanium mesh is liquid PMMA, which is used alone for small defects and/or in conjunction with titanium mesh for larger defects. It is affordable, time-tested and easy to use. However, on-table manipulation often results in some form of craniofacial asymmetry and a post-operative appearance which is suboptimal. Furthermore, the difficult shaping process may take significant time (i.e., up to 80 minutes), which in turn increases anesthesia, total blood loss, risk for infection, morbidity, and all costs associated with longer operative times. In addition, titanium mesh onlay reconstruction—which is one of the most common methods currently utilized—requires overlapping and therefore its sharp, irregular edges may easily extrude and/or pierce the scalp over time, especially in the setting of post-operative irradiation.

With the advent of computer-aided design/manufacturing (CAD/CAM) and customized craniofacial implants (CCIs), more suited alternatives are becoming available. With CAD/CAM fabrication, near-perfectly shaped CCIs can be ordered and pre-fabricated based on fine cut preoperative computed tomography (CT) scans and three-dimensional reconstruction (+/−stereolithographic models). In fact, recent reports suggest that CCI's have the ability to improve cosmesis, decrease operative times and enhance patient satisfaction, if altered for exact reconstruction in real-time during "single-stage" cranioplasty reconstruction."

For example, preoperative imaging such as CT may be used to identify the patient anatomy ahead of time, but the exact defect size following tumor resection is unknown. To follow true oncological principles and to make sure the surgeon is unrestricted in removing all concerning areas of disease (thereby decreasing all risk of recurrence), the prefabricated implant must be able to accommodate the unexpected three-dimensional defect and size, rather than the defect accommodating the prefabricated implant with use of a cutting guide; this is currently being done as a suboptimal solution. As such, the pre-operative CT scan images are used to virtually plan the surgical cuts in an oversized area around the skeletal tumor with excess of several centimeters based on exact location and to allow the geometric design of the three-dimensional (3D) CCI to be created in an "oversized" fashion". In so-called "single-stage cranioplasty", the pre-fabricated custom implant with excess dimensions is designed to account for any additional bone/soft tissue that may become necessary to remove during the surgery (i.e., due to unanticipated local invasion, desire to decrease risk of recurrence and enlargement of resection limits, an unknown tumor pathology grade until resected and sent for frozen analysis with pathology, etc.). Therefore, after resecting the bony/soft tissue region of interest, the surgeon is forced to shave down and modify the oversized CCI to fit exactly within the resected area. However, this type of real-time, intraoperative, manual modification of the oversized custom implant is altogether "labor-intensive", "technically-demanding", and "time-consuming," and is still not perfect for fitting when modified by hand-eye calibration.

Thus, CAD/CAM technology adds another dimension to the material chosen for reconstruction, for example, by allowing one to match the contralateral, non-operated side for ideal contour and appearance. Yet, in the literature, there are only a few case reports where immediate reconstructions with CCI's have been performed for benign skull neoplasms following resection (i.e., meningioma, fibrous dysplasia). While these isolated case reports have reported favorable results and acceptable outcomes, there is a trend towards decreased operative times, and less overall surgery by avoiding risk for revision surgery. In cases of malignant neoplasms involving the bony calvarium, secondary cranioplasty (after surgical margins have been cleared) is currently advocated. However, as of 2014, there was only one successful case report of immediate CCI reconstruction following resection of a Ewing sarcoma.

Historically, cranioplasties with such CCIs can only be performed as second stage operations during which a clinician, such as a surgeon, ensures that the CCI fits perfectly into the skull defect. The recent developments by the inventors and others have demonstrated the feasibility of CCIs for "single-stage cranioplasty", but this involves using a handheld bur to shave down the pre-fabricated implant artistically. However, as described above, challenges in both assessing and predicting each tumor-resection deformity pre-surgery still limits the applicability of CCIs in this patient population. For example, challenges such as 1) unknown exact tumor size, 2) unknown growth from time of pre-op CT scan-to-actual day of surgery, and 3) the amount of unknown resection margins needed to minimize local recurrence. For these cases, the CCI would need to be reshaped/resized intraoperatively in real-time from a size slightly larger than expected; this process may take between 10-80 minutes.

Accordingly, use of a computer-assisted surgical system of an embodiment and a robot/cutting machine for implant modification may significantly reduce the intraoperative time used for reshaping/resizing the customized implant. However, with no established planning/execution systems and/or robots available to assist these single-stage reconstructions, a technology and/or surgical method that allows surgeons to resize, adjust, modify or trim alloplastic or bio-engineered implants during surgery to fit the surgical cuts, defects, and/or pre-existing deformities requiring complex reconstruction, or generally overcome the limitations of current technology and surgical methods, would be welcome in the art.

SUMMARY

In an embodiment, there is a method for forming an implant with an autonomous manufacturing device. The method includes accessing a first computer-readable reconstruction of a being's anatomy; accessing a second computer-readable reconstruction of an implant; accessing a third computer-readable reconstruction comprising the first computer-readable reconstruction superimposed with the second computer readable reconstruction; generating at least one computer-readable trace from a point cloud; and forming an implant with an autonomous manufacturing device, wherein the autonomous manufacturing device forms the implant into a shape defined by at least one dimension of the computer-readable trace.

An advantage of at least one embodiment provides an automated resizing/modification process of the custom craniofacial implant (CCI) with improved accuracy and speed by robot assistance, thereby improving final implant-to-bone relation/position (i.e., reconstructive outcome). At the same time, this significantly reduces the total operative time and unnecessary risks related to prolonged anesthesia. Accordingly, practice of such embodiments would save significant operating room expenses for the hospital associated with prolonged operative times and will accompany reduced potential for surgery-related complications such as implant-to-bone malpositioning/misfit, increased blood loss during time for additional/slower implant modification, accompanying peri-operative morbidity, etc.

Another advantage of at least one embodiment provides a method for forming an implant that provides for a much less time-intensive process, thereby significantly decreasing prolonged operative times/anesthesia requirements, total operating room/surgery-related costs, and all accompanying morbidity related to prolonged surgery/anesthesia (i.e. decreased blood loss)

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 7A shows a left-sided, posterior, full thickness skull defect outlined by a cut region.

FIG. 7B illustrates a pre-fabricated, custom craniofacial implant (CCI) with over-sized dimensions designed virtually using pre-operative CT scan images, including a trace provided by a computer-assisted planning/execution system depicting planned cuts to be made in order to form a resized CCI, for example, by robot/cutting machine (R/CM) and/or surgeon.

FIG. 7C shows a resulting single-stage, CCI-based cranioplasty reconstruction according to an embodiment with a resized CCI attached to a being's anatomy with rigid fixation employing titanium plates/screws, with an exact fit and absent gaps along the periphery of the "implant-cranial bone interface."

FIG. 8 is a pictorial flow chart that illustrates a system and a method for resizing an implant, for example, using an autonomous manufacturing device, such as a robot/cutting machine.

DESCRIPTION OF THE EMBODIMENTS

Figure 1A:
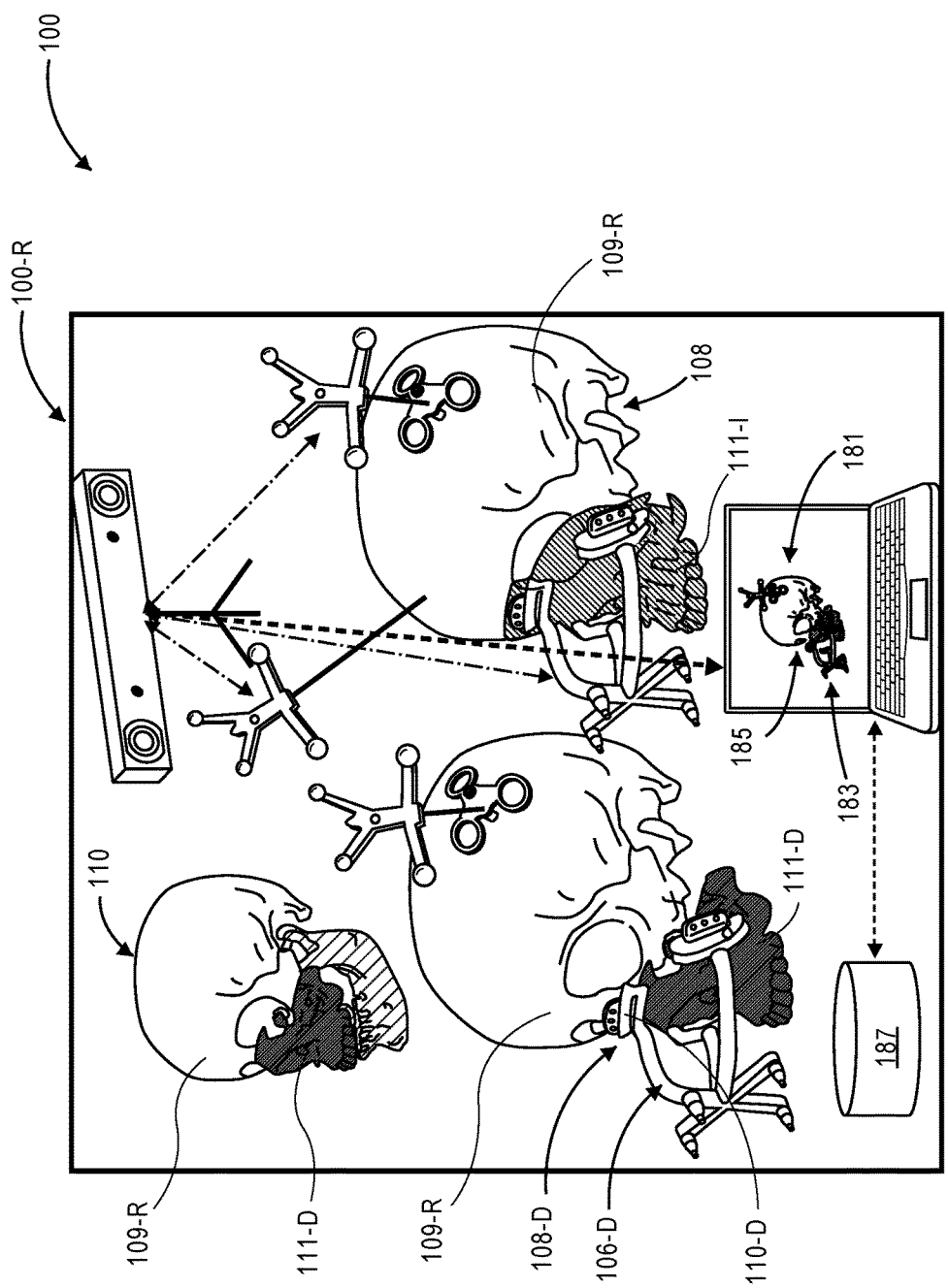
FIGS. 1A-1C provide schematic overviews of a computer-assisted surgical system.
Figure 1B:
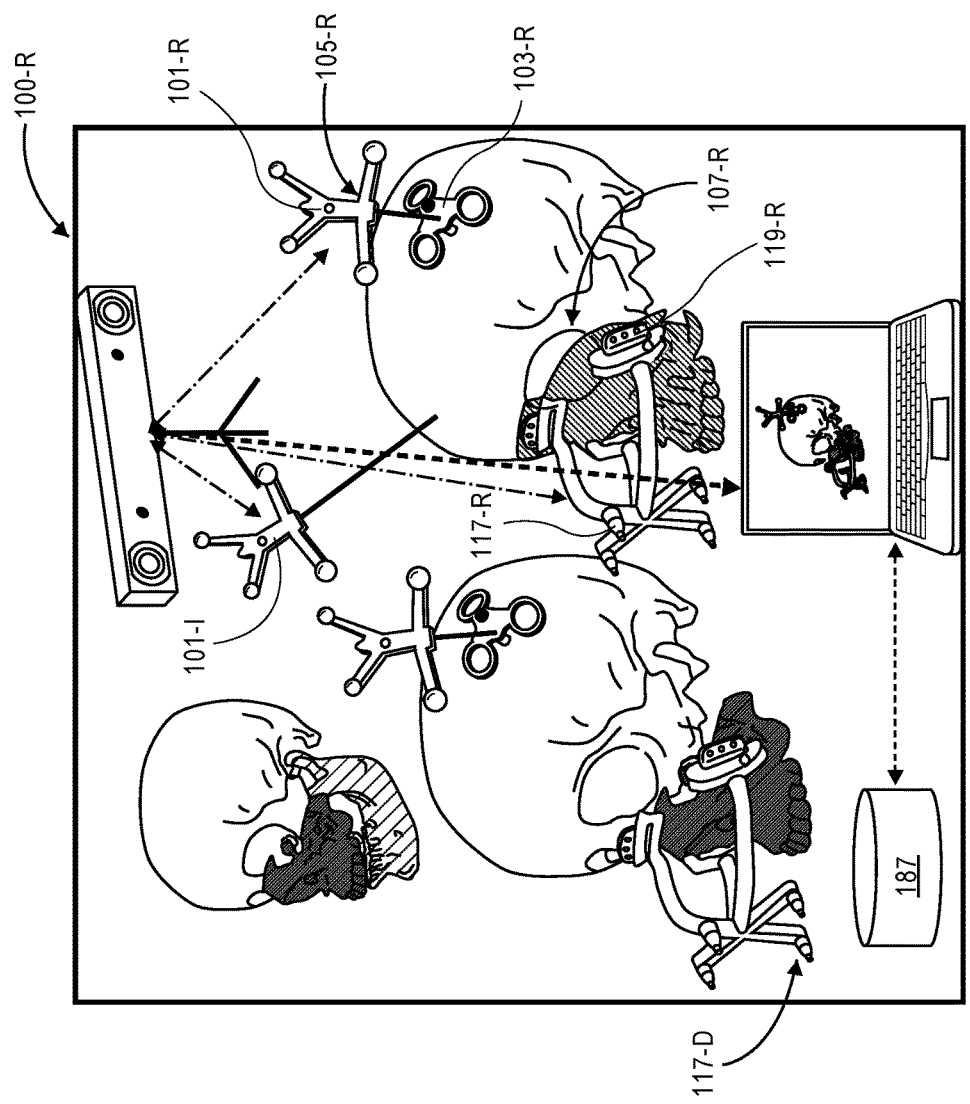
Figure 1C:
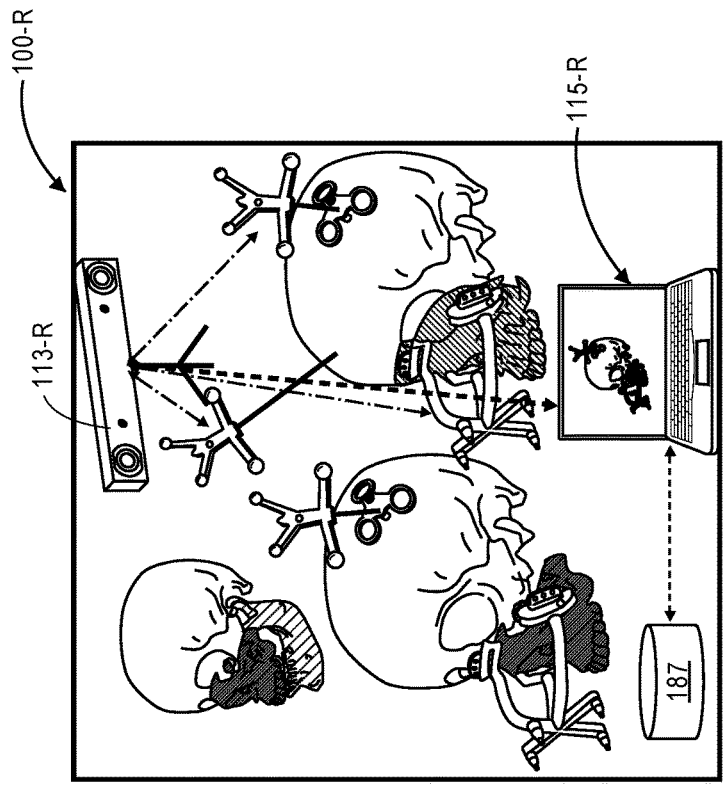
Figure 1D:
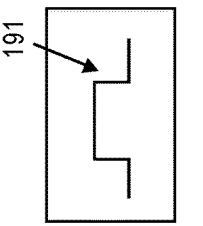
FIGS. 1D-1H are graphical reconstructions of some components and/or features of the surgical system of FIGS. 1A-1C.
Figure 1E:
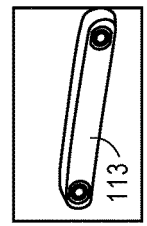
Figure 1F:
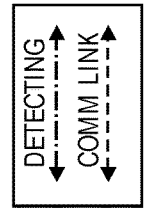
Figure 1G:
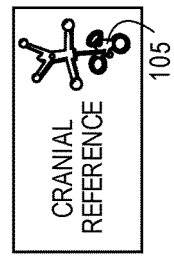
Figure 1H:
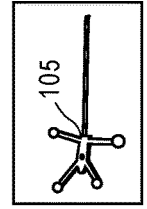

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

In cranioplasty, surgeons rebuild or reconstruct portions of the craniomaxillofacial skeleton to correct deformities (e.g., following trauma) and/or defects created by tumor extirpation. Preoperative imaging such as CT or Mill identifies the patient anatomy. The surgery is planned using virtual pre-operative imaging to help identify an area of interest (e.g., the tumor) requiring reconstruction. Bony cuts are planned and/or created virtually and the implant is designed to fit into the resected region following planned modification of CCI (and is therefore oversized by around 1-3 cm along the periphery). In single-stage cranioplasty, the custom implant has been ordered and delivered with oversized dimensions to account for additional bone that may be removed during the operation. After resecting the bony region of interest, the surgeon shaves down the oversized implant to fit into the resected area. In embodiments described herein, there are methods and devices, including robot assistance, for reducing the time necessary for reducing the size of an implant for better sizing relative to the removed bone. The methods rely on the use of a computer-assisted surgery system (here, a "CAS" system) and/or robotic platform with a 3D scanner.

A CCI may be either supplied by a third-party vendor, printed with an additive or subtractive manufacturing device, such as a 3D printer, that receives instructions generated provided by a system of the embodiments, as described below, so that a custom implant is available to the surgeon and placed utilizing three-dimensional feedback from the CAS system to achieve ideal implant shape/positioning and to align perfectly within the native anatomy. An embodiment of the CAS system described above can be used to provide the clinician with a method for automating the resizing/implant modification with both improved accuracy and significant time reduction by way of a robot/cutting machine, therefore saving substantial expenses associated with prolonged operative times (at an approximate cost to hospital of $100/minute for operational expenses during live surgery) and potential surgical complications related to improper implant-bone defect reconstruction and prolonged anesthesia. Also, the CAS system can access computer-readable reconstructions of a being's anatomy, such as computer-readable files uploaded pre-operatively containing soft tissue and/or skeletal CT scan data, which may be uploaded ahead of time into a memory of a computer incorporated within the CAS system, and which can then be utilized to by a clinician attempting to predict a patient's appearance during and after surgery. In other words, the geometry of interest (i.e., the bony defect within the craniomaxillofacial skeleton) is obtained using any available imaging/tracking modality (e.g., 3D position sensors, optical trackers, electromagnetic tracker, still camera images, depth sensors, video, etc.). The 3D model of the geometry is then transferred to either a robot or small machining active mechanism (herein referred to this as Robot/Custom Machine (R/CM)) that holds the implant within a sterile environment—this is similar to a surgeon modifying an implant by way of "red-light beam" tracer guidance. Next, the 3D geometry obtained from the patient's anatomy of interest in real-time following tumor resection (e.g., anatomical defect's size/shape) can be transformed onto the preoperative images used to fabricate the original custom craniofacial implant (CCI) (and, accordingly, the implant) by applying any registration technique (e.g., point-to-point or point-to-surface registration techniques, such as an Iterative closest point (ICP) technique). This information is provided in files accessed by, for example, the R/CM computer and/or CAS system. The R/CM (i.e., robot) will then automatically cut the implant to the required size intraoperatively with exact dimensions acquired from the patient's anatomy of interest. In another embodiment, a master R/CM can be directly used to digitize the cuts/meshes of anatomy of the interest. This data is then used directly to control a slave R/CM for resizing the CCI.

Various ones of R/CM designs may be selected for the resizing procedure related to "single-stage, implant-based cranioplasty reconstruction" and various other areas within "robot-assisted craniomaxillofacial surgery". For example, the R/CM can either be a robotic arm with an attached cutting tool, a very small parallel robot-like delta and Stewart mechanism robot, or a CNC machine with 3 or 4 axis of movement. The cutting tool that can be used within may be any of these aforementioned machines including a mechanical cutter similar to cutters used in surgery, common machining processes (in lathe or milling machines), and/or a laser cutter.

At least some embodiments described herein can be used for the immediate surgical repair of large cranial defects (e.g., >5 cm$^2$). For example, embodiments described herein may be used for designing, forming, modifying and/or implanting customized craniofacial implants following benign/malignant skull neoplasm (tumor) resection (i.e., referred to as "single-stage implant cranioplasty").

For example, at least some embodiments provide visualization related to a tumor, the resulting skull defect, and the reshaped implant for exact positioning. In other words, in an embodiment, a CAS system can be used for improving both the pre-operative planning and intra-operative execution of single-stage implant cranioplasties.

As described above, cranioplasties may be performed to reconstruct large defects following stroke, trauma, aneurysmal bleeding, bone flap removal for infection, and oncological ablation. With this in mind, embodiments described herein include a computer-assisted algorithm that may be used for reconstructing tumor defects with pre-CCIs for an ideal result.

Accordingly, embodiments described herein may be used by surgeons in performing single-stage cranioplasty following oncological resection. In other words, embodiments include algorithms for real-time updates related to single-stage customized implant cranioplasty. For example, in an embodiment, a CAS system, which is a single, seamless platform capable of being used for both pre planning (pre-op use) and navigation (intra-op use), overcomes the limitations of conventional systems that do either one or the other. In addition, embodiments include novel hardware such as a rigid cranial reference mount.

A computer-assisted surgical system, such as the system described herein, may be utilized for the pre-operative planning and intra-operative execution of a single-stage implant cranioplasty. For example, in a single-stage implant cranioplasty, the anatomy of a being, which may be a human being, may include an anatomical feature, such as a diseased portion of the anatomy that requires removal or replacement with an implant. During a surgical procedure, the anatomical feature may be separated from the being by cutting away from healthy portions of the being's anatomy. Subsequently, an implant, such as a customized craniofacial implant, which may be fabricated via additive or subtractive manufacturing technology, may be attached near the healthy portions of the being's anatomy via an attachment.

A computer-assisted surgical system, such as the system 100 is depicted in FIGS. 1A-1G. System 100 may be utilized, for the pre-operative planning and intra-operative execution of a single-stage implant cranioplasty 100-R instead of (or in addition to) transplantation. For example, in a single-stage implant cranioplasty, the anatomy of a being 108, which may be a human being, may include an anatomical feature 111-D, such as a diseased portion of the anatomy, that requires removal or replacement with an implant 111-i. During a surgical procedure, the anatomical feature 111-D may be separated from the being 108 by cutting away from healthy portions 109-R of the being's anatomy. For example, a custom-made cutting guide 106-D may be used to provide a surgeon with slots that provide access for a cutting tool at preselecting cutting locations along the being's anatomy. After cutting sufficiently through the being's anatomy at the locations specified by the cutting guide 117-D, the anatomical feature is removed away from the being. Subsequently, an implant, such as a customized craniofacial implant 111-I, which may be fabricated via additive or subtractive manufacturing technology, may be attached near the healthy portions 109-R of the being's anatomy via an attachment 119-R.

System 100 may include a reference unit 105-R, an implant 111-I and a detector 113-R. The reference unit 105-R may include a first trackable element 101-R. The implant may include a second trackable element 101-I. The implant 111-I may include an attachment 119-R which may have a contoured attachment surface 107-R. In addition to, or instead of trackable element 101-R, the attachment 119-R may also include one of a second trackable element 117-R. The detector may be configured to provide at least one signal 191 corresponding to a detected location of at least one of the first trackable element 101-R and the second trackable element 117-R. Reference unit 105-R may include a cranial reference mount 103-R that may be attached to a location 110 of a being's anatomy to provide a static frame of reference for tracking the location of first trackable element 101-R.

The system 100 may further include a cutting guide 106-D having a third trackable element 117-D, and may be detected by the detector 113-R. Thus, the at least one signal 191 may further correspond to a detected location of at the third trackable element 117-D of the cutting guide 106-D. The cutting guide 106-D may be a surgical guide assembly having an attachment device 108-D configured to be coupled to a bone. A cut location indicator 110-D may be coupled to the attachment device. The cut location indicator identifies a location where the bone is to be cut. The support structure may be configured to have the third trackable element 117-D coupled thereto.

The system 100 may also include at least one computer 115-R, that receives the at least one signal 191 from detector 113-R, may also include an additive manufacturing device 187, which may be in communication with and controlled by the computer 115-R. The computer may be connected to a display on which computer-readable reconstructions of items, such as the implant and a being's anatomy, may be displayed. The at least one signal 191 may be communicated between the detector and computer via a communications link, which may include data transmission wires and/or wireless transmissions either of which may be communicated through a network, such as a LAN or WAN network, including communication over an intranet or over the internet, including TCP/IP data transfer. The at least one computer 115-R may be selected from a desktop computer, a network computer, a mainframe, a server, or a laptop. The at least one computer may be configured to access at least one computer readable reconstruction of at least one object, such as a being's anatomy, or at least portions of the being's anatomy, for example, a first computer readable reconstruction 181 and a second computer readable reconstruction 185, and a third computer readable reconstruction. The computer readable reconstruction may include three-dimensional (3D) views, such as those created by scanning a patient via, for example, CT scan. At least one display may be connected to the at least one computer 115-R. The display may be configured to represent the computer readable reconstruction in a format visible to a user. The first computer may include at least one memory to store data and instructions, and at least one processor configured to access the at least one memory and to execute instructions such as instructions included in software files.

The detector 113-R may be an optical tracker, a magnetic tracker or both an optical tracker and a magnetic tracker. Optical trackers typically emit and capture light in the invisible (infrared) electromagnetic spectrum. Trackable fiducials (i.e., the trackable elements) used with these systems can include passive (i.e., reflective) or active (i.e., those that actively emit infrared light) markers. Using specific geometries known to the camera, the pose of a reference can be tracked through a field of view (as indicated by the dash-dotted lines). An example system is the NDI Polaris available from Northern Digital, Inc. (Ontario, Canada). Magnetic trackers rely on a magnetic field generator and (typically) a passive coil architecture. The field generator creates a time-varying field, which induces a current in the passive sensor. This current is measured and, through a calibration procedure, used to identify up to a 6-dof pose of the sensor. An example system is the NDI Aurora available from Northern Digital, Inc. (Ontario, Canada).

One or more of the first trackable element 101-R, the second trackable element 101-I, and the third trackable element 117-D, may be an IR reflector or an IR emitter, each of which may be detachably connected to an attachment surface. As an example, an IR reflector may be a detachably connected surface, such as a sphere. As an example, an IR emitter may be a light emitting diode configured to emit infrared light.

The implant 111-I may be fabricated during a surgical procedure by an additive or subtractive manufacturing device, or may be a pre-fabricated implant such as a $3^{rd}$-party sourced alloplastic implant, including a customized craniofacial implant (CCI) implant. In an embodiment, the implant may include a polymer, metal, bioengineered material, or combinations thereof. For example, the implant may include titanium mesh, porous hydroxyapatite (HA), polymethylmethacrylate (PMMA), polyether ether ketone (PEEK) and/or combinations thereof.

Figure 2:
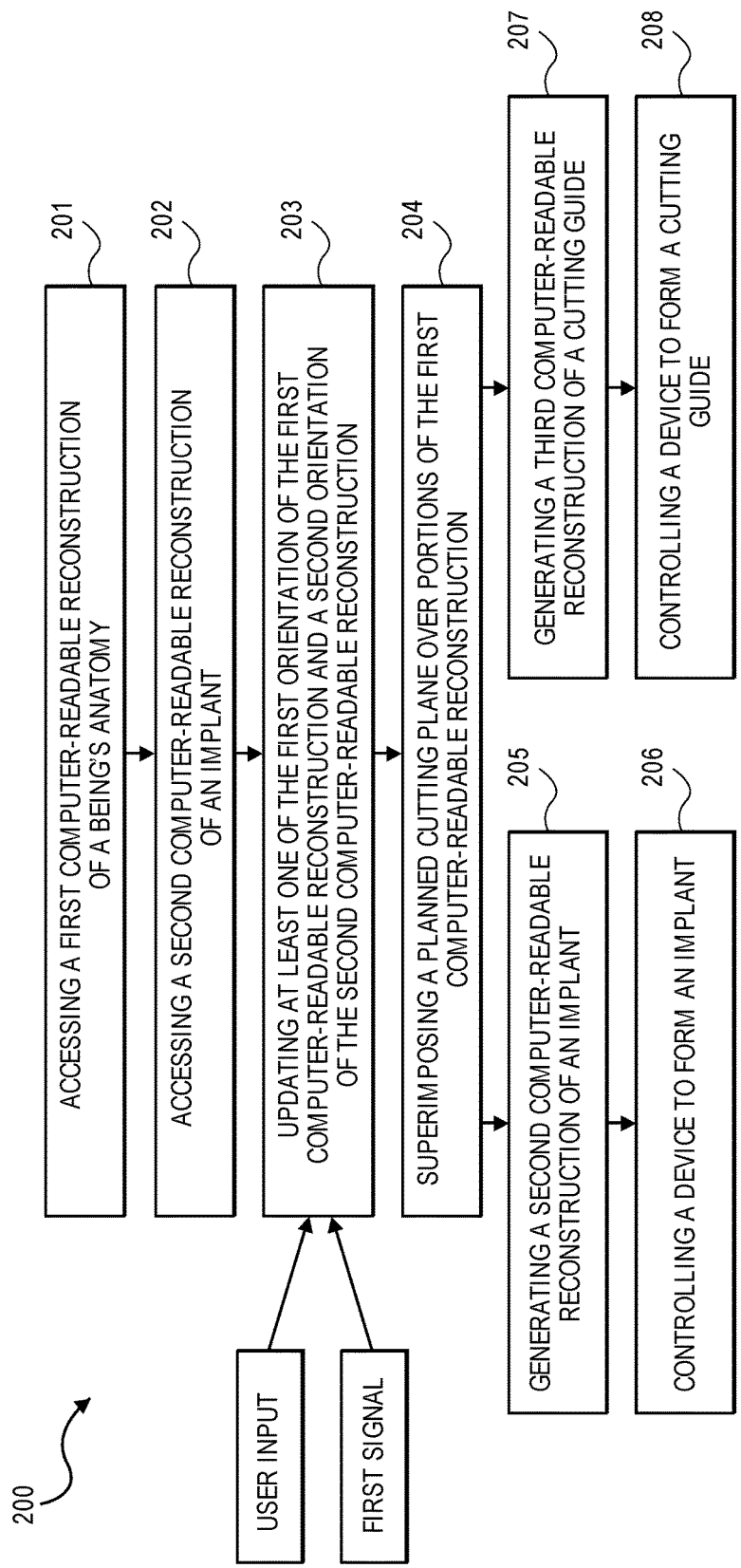
FIG. 2 is a flowchart depicting representative steps for executing a method of an embodiment.

The first computer may include at least one memory to store data and instructions, and at least one processor configured to access the at least one memory and to execute instructions, such as instructions 200 included in the flow chart in FIG. 2. Instructions 200 may include one or more of the steps included in the flowchart on FIG. 2. For purposes of providing examples, some of the steps are described below with reference to components of system 100 from FIGS. 1A-1G.

In an embodiment, first instructions 200 include accessing a first computer-readable reconstruction of a being's anatomy at 201 and accessing a second computer-readable reconstruction of an implant at 202. The first computer-readable reconstruction of the being's anatomy may include a first updatable orientation and the second computer-readable reconstruction of the implant may include a second updatable orientation.

During a surgical procedure, such as an implantation of an alloplastic, metal and/or bioengineered implant onto the craniomaxillofacial anatomy of a patient being's anatomy (i.e. head or face), it is useful to track the location of the implant relative to the anatomy of the patient being before, during and/or after the implantation. Accordingly, a signal—such as signal 191 in the system 100—may correspond to a location of the first, second and/or third trackable element as detected by the detector 113. Thus, the instructions 200 may also include updating the orientation of the first, second and/or third computer-readable reconstruction of the implant with an orientation that is updated based on the signal, which may correspond to a physical location of the first, second and/or third trackable element, respectively, as sensed by the detector. For example, at 203, the instructions 200 may also include updating at least one of the first (updatable) orientation and the second (updatable) orientation. In an example, step 203 may be initiated by user input, for example, via user interaction with the computer, or by a signal, such as a signal provided by a detector. As described above, the first orientation and the second orientation may be updated, for example, on a display connected to the computer, in response to the at least one signal.

The instructions 200 may include superimposing a planned cutting plane over portions of the first computer-readable reconstruction at 204. Other steps may include generating a second computer-readable reconstruction of an implant at 205 and controlling an additive manufacturing device at 206 to form an implant. In an example, the second computer-readable reconstruction of the implant generated at 205 may include a geometry defined by at least one of: i) an interface between the planned cutting plane and the first computer-readable reconstruction, and ii) a selected portion of the computer-readable reconstruction, the selected portion comprising an anatomical feature of the being's anatomy, including but not limited to oncological defect sites, such as a benign/malignant skull neoplasm, large defects following stroke, trauma, aneurysmal bleeding, bone flap removal for infection, and oncological ablation. Additionally, the implant fabricated by the manufacturing device at 206 may have dimensions defined by the geometry of the second computer-readable reconstruction.

The instructions 200 may also include generating a third computer-readable reconstruction of a cutting guide at 207 and controlling the additive manufacturing device to form a cutting guide at 208. In an example, the third computer-readable reconstruction of the cutting guide may include a geometry defined by an interface between the planned cutting plane and the first computer-readable reconstruction, and may also include a third updatable orientation. Additionally, the cutting guide fabricated by the manufacturing device at 208 may include selected dimensions of the geometry of the third computer-readable reconstruction.

The device may be any manufacturing device that fabricates an object based on instructions, such as computer readable instructions, for example, instructions provided in digital data, including any device that utilizes additive or subtractive manufacturing technologies, such as those that fabricate an object from appropriately approved materials for medical use. Accordingly, the at least one device may be an additive manufacturing device, such as a 3D printer, or another kind of manufacturing device, including subtractive manufacturing device, such as a CNC machine. Examples of additive manufacturing technologies may include vat polymerization (e.g., PROJET® 6000, 7000, 8000 available from 3D Systems Corp., Rock Hill, S.C.), materials jetting (e.g., Objet 500 or Eden 250, each available from Stratasys, Ltd., Eden Prairie, Minn.), powder binding (e.g., PROJET® 460, 650 available from 3D Systems Corp., Rock Hill, S.C.), powder fusion (e.g., EBM® available from Arcam AB, Sweden), material extrusion (Fortus 250, 400, available from Stratasys, Ltd., Eden Prairie, Minn.), or any one denoted by the ASTM F42 committee on additive manufacturing. Accordingly, system 100 may include a device (not shown) for manufacturing components, such as cutting guides, reference units and/or the trackable elements, and the device may be connected to the at least one first computer via the communications link described above. The instructions may also include generating a computer readable file that contains instructions for manufacturing the cutting guide and/or implant, for example a computer readable file that contains dimensions of a component, such as a cutting guide based on the geometry of the third computer-readable reconstruction. The computer-readable reconstruction of the being's anatomy may be a computer-readable file created from a CT-scan. For example, the computer-readable reconstruction may be a 3D reconstruction of a patient's anatomy.

In an embodiment, there is also a computer-assisted surgical method. The method includes use of the computer-assisted surgery system, which may provide a user enhanced implant reconstruction experience, for example, providing a surgeon unprecedented, immediate visual feedback and allowing single-stage implant cranioplasty and all related craniomaxillofacial reconstruction for scenarios related to skull neoplasms, etc—in situations where the tumor defect is not known beforehand, but where a customized implant is needed requiring on-table modification via computer-assisted surgery system guidance.

Generally, the method can include the following: a) generating and/or accessing a computer-readable reconstruction of a patient's anatomy, such as via a preoperative CT scan that includes an anatomical feature, such as a defect, and constructing a 3D model of the anatomy; b) preselecting a resection area on the model; c) determining implant dimensions (can be a few millimeters greater than the size of the defect) and fabricating the implant with an additive and/or subtractive manufacturing device incorporated with the computer-assisted surgery system; d) designing a trackable cutting guide based on the 3D model and fabricate with an additive and/or subtractive manufacturing device incorporated with the computer-assisted surgery system; e) attaching a reference unit having a trackable element onto the patient's anatomy, such as at the patient's skull; f) registering the location of the trackable element/reference unit to the computer-readable reconstruction (preoperative CT scan); g) using the optically trackable cutting guide to perform bone cuts in the patient; h) using a detector to generate a signal in response to performing a trace of the defect boundaries, for example, if additional resection is required; i) superimposing information corresponding to signals generated by optical digitizer, such as signals in response to performing a trace of the defect boundaries, on the computer-readable reconstruction; j) registering the implant to the computer-readable reconstruction with the optical digitizer, for example, via tracking a location of a trackable element attached to the implant; k) tracing cut lines on the implant based on information obtained from the 3D model, such as a size mismatch between the implant and the defect; l) attaching the implant to the patient; m) obtaining a post-operative image of the patient and the attached implant, such as a CT scan.

The method may include any step or combination of steps included in the flow charts of FIG. 3-4 and described below. In an example shown in the flow-chart of FIG. 3, with reference to the features of the system 100 in FIGS. 1A-1H, a method 300 can include attaching a reference unit that includes a first trackable element to a first anatomical feature of a being's anatomy at 301. The method may also include detecting a location of at least the first trackable element with a detector at 302, and accessing a first computer-readable reconstruction of the being's anatomy at 303. The detector may be detector 113 as described above, and may be configured to provide at least one signal corresponding to a detected location of at least the first trackable element. The first computer-readable reconstruction may be first computer-readable reconstruction 181 and may include a first updatable orientation. Accordingly, the first updatable orientation may be updated in response to user input and/or the at least one signal such as signal 191 described above.

Figure 3:
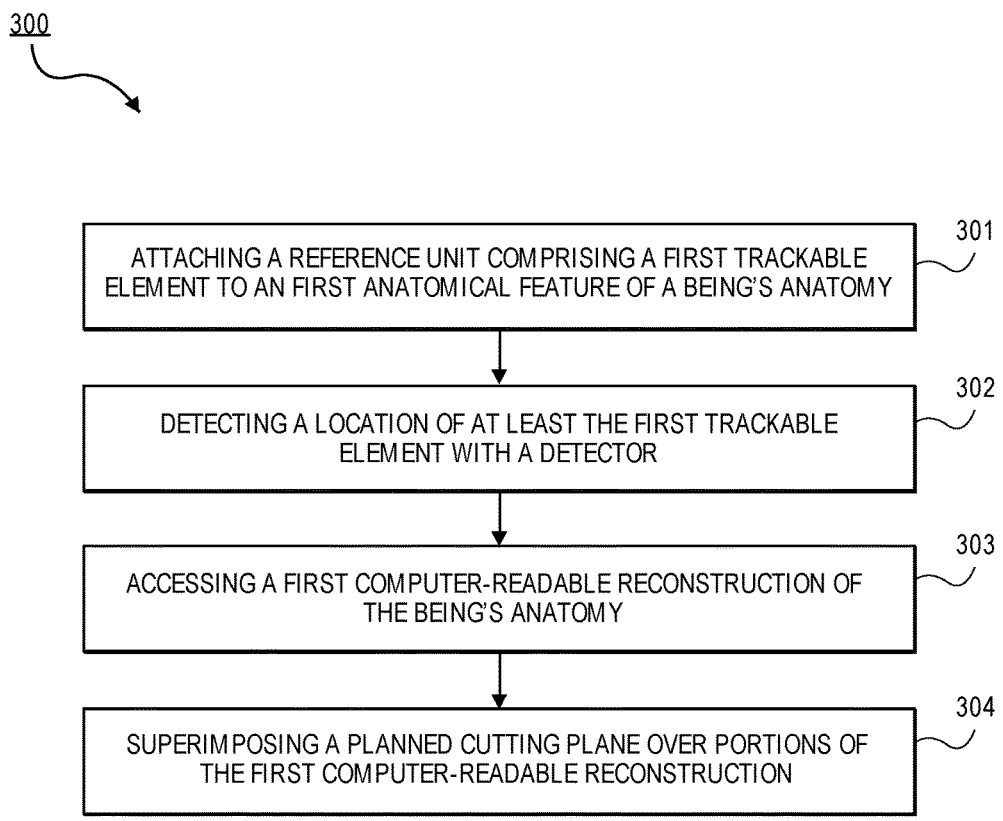
FIG. 3 is a flowchart depicting representative steps for executing a method of an embodiment.
Figure 4:
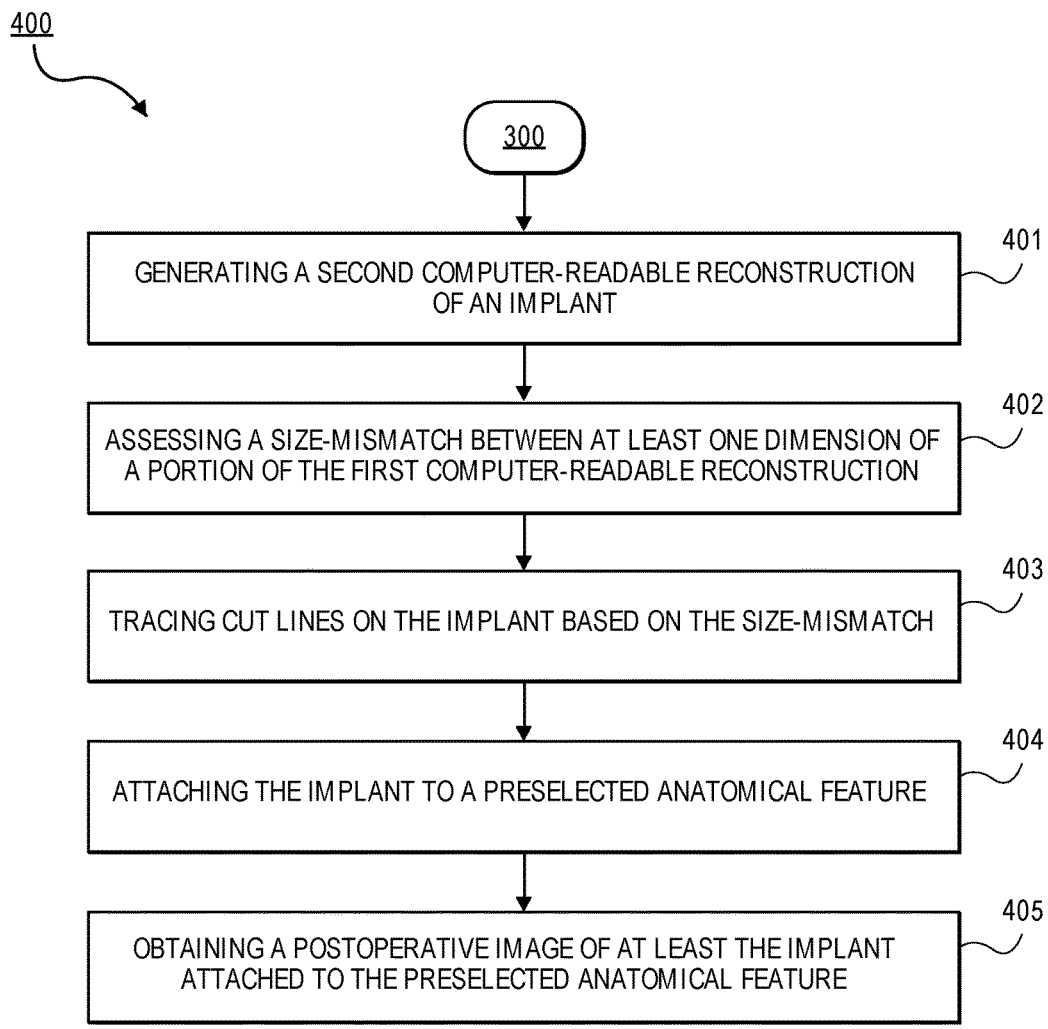
FIG. 4 is a flowchart depicting representative steps for executing a method of an embodiment.
Figure 5:
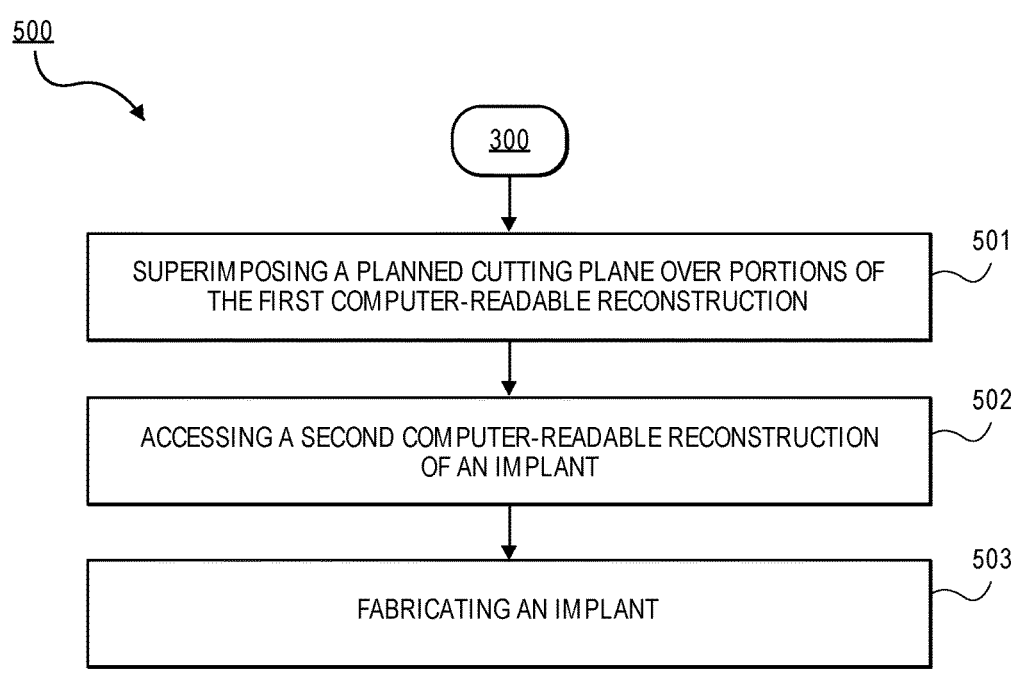
FIG. 5 is a flowchart depicting representative steps for executing a method of an embodiment.

In an embodiment, a method 400 may include all of the steps 300 of FIG. 3 and may also include any step or combination of steps included in the flow charts of FIGS. 3-5. In an example shown in the flow chart of FIG. 4, in addition to method 300, method 400 may include generating a second computer-readable reconstruction of an implant at 401. The second computer-readable reconstruction may be second computer-readable reconstruction 185 as described above, and may include a second updatable orientation, such as an orientation that may be updated in response to user input and/or the at least one signal, such as signal 191 described above. The method 400 may also include assessing a size-mismatch between at least one dimension of a portion of the first computer-readable reconstruction, for example, a portion corresponding to a selected anatomical feature of the being's anatomy, and at least one dimension of the second computer-readable reconstruction at 402. In an example, assessment of the size-mismatch may be performed via a cephalometric analysis, including a real-time cephalometric analysis. The method 400 may also include tracing cut lines on the implant based on the size-mismatch. In an example, the cut lines may be traced on the implant such that an anatomical discrepancy at an area of removal or reconstruction of the anatomical feature is minimized. In an example, the anatomical discrepancy may be minimized based on a preselected tolerance, for example, in instructions provided for fabricating the implant, including instructions provided in computer-readable files, such as digital data, provided to an implant manufacturing device. The method 400 may also include attaching the implant to a preselected anatomical feature at 404, such as to a patients anatomy surrounding oncological defect sites, such as a benign/malignant skeletal neoplasm, or large defect sites formed following stroke, trauma, aneurysmal bleeding, bone flap removal for infection, and oncological ablation. After implantation of the implant at 404, for example, the method can also include obtaining a post operative image of at least the implant attached to the preselected anatomical feature at 405. For example, a CT scan may be taken of the patient with implant attached.

In an embodiment, a method 500 may include all of the steps 300 in FIG. 3, and may also include any step or combination of steps included in the flow charts of FIGS. 3-5. In an example shown in the flowchart in FIG. 5, in addition to method 300, method 500 may include superimposing a planned cutting plane over portions of the first computer-readable reconstruction at 501. In an example, the planned cutting plane may be superimposed to bisect the first computer-readable reconstruction to define at least one portion of the first-computer readable reconstruction corresponding to at least one diseased anatomical feature of the being's anatomy that is to be removed or replaced. Accordingly, the planned cutting plane may be planned cutting plane as described above, and the first computer-readable reconstruction may be the first computer-readable reconstruction 181 as described above. The method 500 may also include accessing a second computer-readable reconstruction of an implant at 502 and fabricating an implant at 503. The second computer-readable reconstruction may be second computer-readable reconstruction 185 as described above, and may include a second updatable orientation, such as an orientation that may be updated in response to user input and/or the at least one signal, such as signal 191 described above. The implant may be implant 111-I described above, and may include dimensions that correspond to the geometry of the second computer readable reconstruction. Additionally, a second trackable element may be provided on the implant. For example, a second trackable element such as trackable element 1014 as described above, may be may be incorporated in the design of the implant as a detachably connected trackable element, or may be formed separate from the implant and attached to the implant. It is noted that the at least one signal, such as signal 191, may also correspond to a detected location of the second trackable element, such as that detected by detector 113. It is also noted that the planned cutting plane may also include a fourth updatable orientation, such as an orientation that may be updated in response to user input.

The described method may be utilized during a surgical procedure, such as a surgical implantation procedure for various forms of craniomaxillofacial surgery including an implant-based cranioplasty. The implant may be a custom, 3D craniofacial implant made of either alloplastic materials or biologic tissue engineered cells as described above for implant 111-I and a being, such as a recipient being, on whom the surgical procedure is performed.

During a surgical procedure, such as an implantation of an alloplastic, metal and/or bioengineered implant onto the anatomy of a patient, it is useful to track the location of the implant relative to the anatomy of the patient before, during and/or after the implantation. Accordingly, the signal—such as signal 191 in the system 100—may correspond to a location of the first, second and/or third trackable element as detected by the detector 113. Thus, the computer-assisted surgical method of the embodiments may include updating the orientation of the first, second and/or third computer-readable reconstruction of the implant with an orientation that is updated based on the signal, which may correspond to a physical location of the first, second and/or third trackable element, respectively, as sensed by the detector.

In an example, the computer-assisted surgery surgical system of the embodiments as described herein can be utilized by a user, such as a surgeon, to quickly and accurately shave down an oversized CCI. Such an oversized CCI may be designed to the curvature specific only to the patient's skull—using information about the intraoperative bony resection following instantaneous, computer-assisted registration. In an embodiment of a surgical method described with reference to FIGS. 6-9, a clinician (for example, a surgeon) digitizes points of the removed anatomical feature, such as a cut region from which bone is removed to correct conditions such as a tumor, and the anatomical defect is assessed in real-time using the computer-assisted surgery system. In other words, a computer of the system accesses first computer-readable reconstruction of a being's anatomy, which may be preoperative surface models of the skull (e.g., segmented from CT). Additionally, a computer of the system may access a second computer-readable reconstruction of an implant, which may be a surface model of the oversized pre-fabricated CCI.

Figure 6:
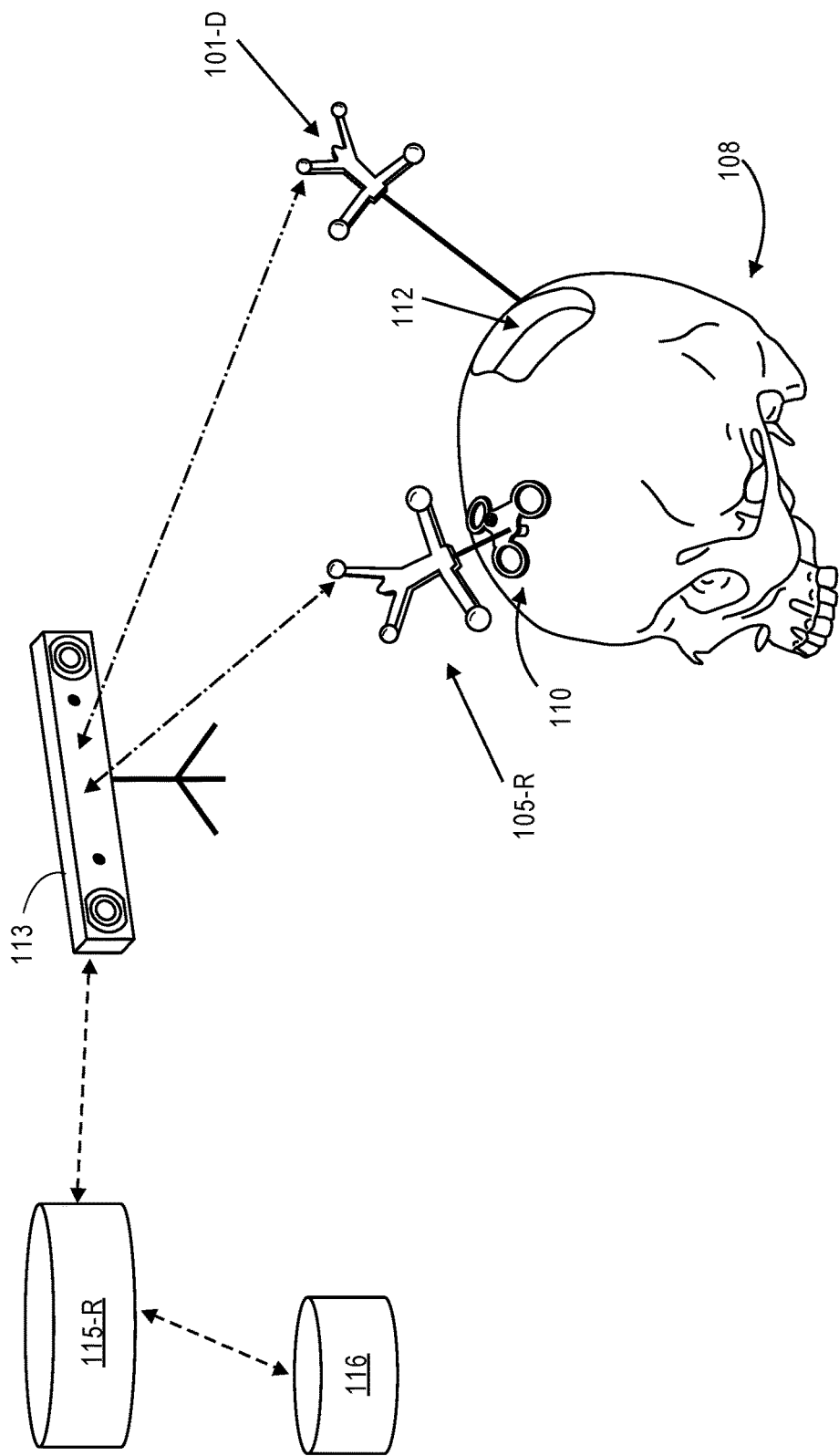
FIG. 6 illustrates an example tracker digitization. A reference geometry is attached to the patient (via a cranial mount, for example) and to a digitizer. A tracking unit, such as an optical tracker, tracks the reference geometries. The digitizer captures the outline of the cut region.

As illustrated in FIG. 6, digitization can be achieved through tracking technology such as an optical (infrared) and/or electromagnetic trackers (detector 113) as in system 100. A trackable pointer tool 101-D with a digitizer (a trackable element) and/or a reference unit 105-R can be tracked by the detector 113. As described previously, the tracker may be a detector that generates signals in response to sensing a trackable element of the trackable pointer tool 101-D and/or of reference unit 105-R. The trackable pointer tool 101-D can be used for tracing a geometry of the region of interest 112, the geometry being digitized and converted into a computer-readable pattern such as a trace. For example, by using a registration between the patient anatomy and patient model (i.e., a computer-readable reconstruction of the patient's anatomy) such as via a location of a static point provided by reference element 105-R, the points from the digitized trace can be transformed to a patient model. In other words, a as the clinician traces the geometry of the region of interest 112, the detector 113 detects an orientation and location of the trackable pointer tool 101-D relative to a location of the reference unit 105-R, generates signals corresponding to the sensed location of the trackable pointer tool 101-D and/or reference unit 105-R and sends those signals to a computer which, in turn, generates a computer-readable reconstruction of the geometry which can be superimposed over a computer-readable reconstruction of the patient's anatomy.

Accordingly, a surgical method can include attaching a reference unit 105-R having a first trackable element to a first anatomical feature 110 of a being's anatomy 108; detecting a location of at least the first trackable element with a detector 113 configured to generate at least one first signal corresponding to a detected location of at least the first trackable element, the generated signal being provided to, for example, a computer 115-R having a memory and a processor for executing instructions. The method may include accessing a first computer-readable reconstruction of the being's anatomy, the first computer-readable reconstruction comprising a first updatable orientation, wherein the first updatable orientation is updated in response to the at least one first signal. The method can also include accessing a second computer-readable reconstruction of an implant, the second computer-readable reconstruction comprising a second updatable orientation. The method may also include detecting a location of at least one second trackable element of, for example, the trackable pointer tool 101-D with the detector 113. The detector may further be configured to generate at least one second signal corresponding to a detected location of at least the second trackable element of the trackable pointer tool 101-D, the second generated signal being provided to, for example, and computer 115-R. Thus, the method may also include generating at least one updatable, computer-readable trace, the trace corresponding to a geometry based on updated location data for the at least one second trackable element of the trackable pointer tool 101-D. The method also includes superimposing the least one updatable, computer-readable trace over portions of the second computer-readable reconstruction of the implant. In an example, a location of the superimposed computer-readable trace may be manipulated based on user input.

In addition to the computer 115-R that receives at least one signal from the detector 113, and the system may also include an additive or subtractive manufacturing device 116, such as an autonomous manufacturing device, for example, an implant material-removal tool such as a robot/cutting machine ("R/CM") which may be in communication with and controlled by the computer 115-R or may have its own onboard memory and process that receives and executes files from the computer. The computer 115-R may be connected to a display (not shown in FIG. 6) on which computer-readable reconstructions of items, such as the implant and a being's anatomy, may be displayed. Then at least one signal may be communicated between the detector, the computer, and/or the R/CM 116, via a communications link. The communications link may include data transmission wires and/or wireless transmissions either of which may be communicated through a network, such as a LAN or WAN network, including communication over an intranet or over the internet, such as TCP/IP data transfer.

The manufacturing device 116 may be any manufacturing device that fabricates an object based on instructions, such as computer readable instructions, for example, instructions provided in digital data, including any device that utilizes additive or subtractive manufacturing technologies, such as those that fabricate an object from appropriately approved materials for medical use. Accordingly, at least one device may be an additive manufacturing device, such as a 3D printer, or another kind of manufacturing device, including a subtractive manufacturing device such as a CNC machine. Examples of additive manufacturing technologies may include vat polymerization (e.g., PROJET® 6000, 7000, 8000 available from 3D Systems Corp., Rock Hill, S.C.), materials jetting (e.g., Objet 500 or Eden 250, each available from Stratasys, Ltd., Eden Prairie, Minn.), powder binding (e.g., PROJET® 460, 650 available from 3D Systems Corp., Rock Hill, S.C.), powder fusion (e.g., EBM® available from Arcam AB, Sweden), material extrusion (Fortus 250, 400, available from Stratasys, Ltd., Eden Prairie, Minn.), or any one denoted by the ASTM F42 committee on additive manufacturing.

Accordingly, the manufacturing device 116 of FIG. 6 may be a device for manufacturing components, such as CCIs, and the device may be connected to at least one of the first computers via the communications link described above. The instructions may also include generating a computer readable file that contains instructions for manufacturing the implant. For example the computer readable file may contain dimensions of a trace, which may define contours of a resected area on a being's anatomy, which may be stored as geometric information in a computer-readable reconstruction of the patient's anatomy of interest. The manufacturing device 116 may then construct the implant from raw material or may remove material of a prefabricated CCI (for example an oversized implant or a block of material) in order to properly size the implant according to the geometry of the trace.

For example, FIGS. 7A-7C illustrate together a schematic application of single-stage cranioplasty reconstruction with CCI and the final result with embedded implant. As shown in FIG. 7A, the resected skull tumor leaves behind an anatomical feature of interest 112, such as a defect with varying thickness which is not consistently smooth due to the manual cutting aspect with craniotome by neurosurgery. A custom craniofacial implant 120 may be designed oversized and a resizing procedure, such as cutting the implant along a trace line 118 shown in FIG. 1B, may be required. A manufacturing device, for example, a cutting tool, such as a robot/cutting machine ("R/CM"), may be utilized for automating the resizing procedure to form a resized implant 120'. The result of such a single-stage cranioplasty reconstruction according to an embodiment is shown in FIG. 7C with the resized implant 120' attached to the being's anatomy 108 and showing an exact fit and is absent of gaps along the periphery of the "implant-cranial bone interface" 112'.

FIG. 8 illustrates a system that can be utilized for automated resizing of an implant using a machine (e.g., a robot) that can resize the implant from images/movies captured intraoperatively. For example, in using such a system an infrared optical sensor arrangement 801 (e.g., a 3D sensor attached to an IPAD® (Apple Inc., California)) captures images of an anatomical feature 802 and creates a computer readable reconstruction 803, such as a 3D image file, corresponding to the anatomical feature, a portion of which that may be used for generating a trace geometry corresponding to, for example, a resected portion of the being's anatomy. The trace geometry information, which may be contained in a computer readable file, may be incorporated with instructions that are read by a controller that controls a manufacturing device 116, such as a robot, for example the robotic arm with attached cutting tool 900 of FIG. 9, parallel robot 1000 of FIG. 10, a computer-controlled tool, a tool attached to a haptic device, a parallel robot in which the robot holds, moves and rotates the implant to a desired position and orientation and wherein the cutting tool position is fixed and only rotates along its axis utilizing a simple motor. The manufacturing device 116 then executes the instructions to, for example, resize the implant according to the trace geometry to provide a properly sized implant 120'.

As discussed above, in a method of an embodiment, an implant may be fabricated during a surgical procedure with a manufacturing device, such as an additive or subtractive manufacturing device, for example, a robot/cutting machine, or "R/CM"). Alternatively, in a method of an embodiment, the implant may be a pre-fabricated implant such as a $3^{rd}$-party sourced alloplastic implant, including a an oversized CCI (i.e., may have at least one dimension that is larger than at least one dimension of the resected surface of the patient's anatomy). The implants of the embodiment may also have static and/or dynamic (i.e., real-time) tracking capabilities included thereon for tracking with a computer-assisted surgical system described above or may be provided with a trackable element attached thereon and/or produced with surface indentations/modifications in order to allow enhanced three-dimensional tracking and implant placement confirmation (as compared to, for example, a virtual plan which may be modeled virtually during a pre-operation exercise.

In an embodiment, the implant may include a polymer, metal, bioengineered material, or combinations thereof. For example, the implant may include titanium mesh, porous hydroxyapatite (HA), polymethylmethacrylate (PMMA), polyether ether ketone (PEEK) and/or combinations thereof. In the case of an oversized implant, the R/CM may be utilized to remove excess implant material from the oversized implant in order to properly size the implant (i.e., to resize the implant during surgery in real-time so that its geometry substantially conforms to a geometry of the resected portion of the being's anatomy).

Figure 9:
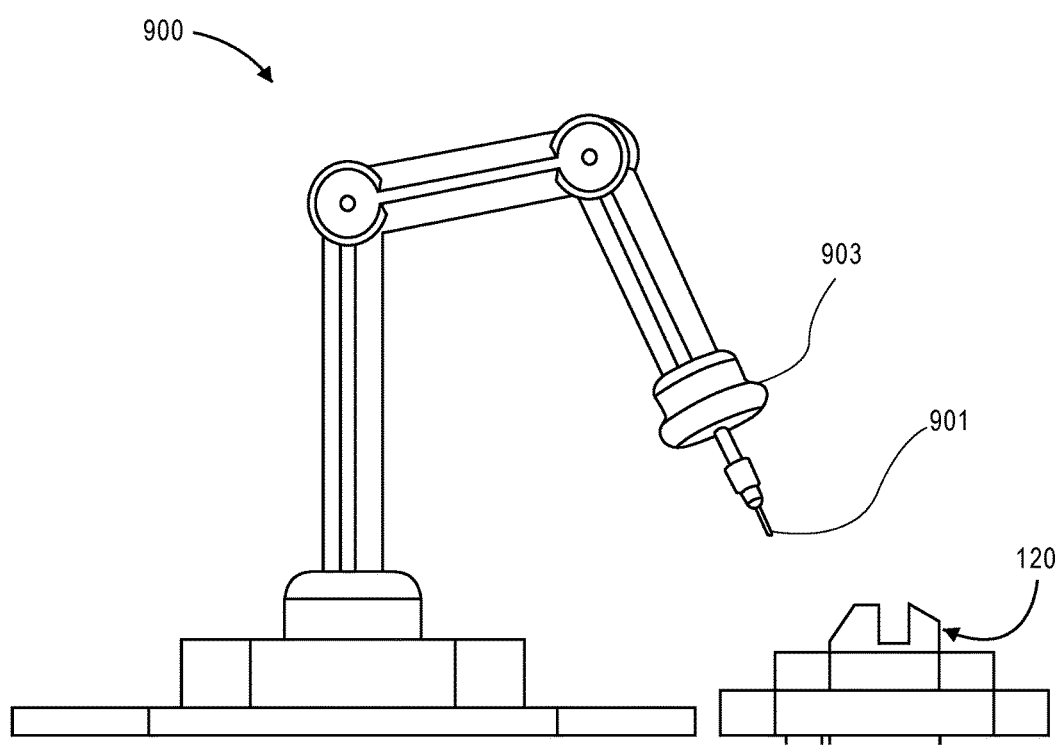
FIG. 9 is an illustration of a representative robotic arm with sufficient degrees of freedom (DOF) and a cutter attached to its end effector. This cutter may be a rotary mechanical or a laser cutter. The robot follows the desired path and orientation of each cutting point.

For example, FIG. 9 shows a representative robotic arm 900 as the manufacturing device 116. An exemplary robotic arm 900 may have sufficient degrees of freedom (DOF) and a cutter 901 attached to its end effector 903. This may be a rotary mechanical cutter or a laser cutter. The robotic arm follows a desired path and orientation of each cutting point.

Figure 10A:
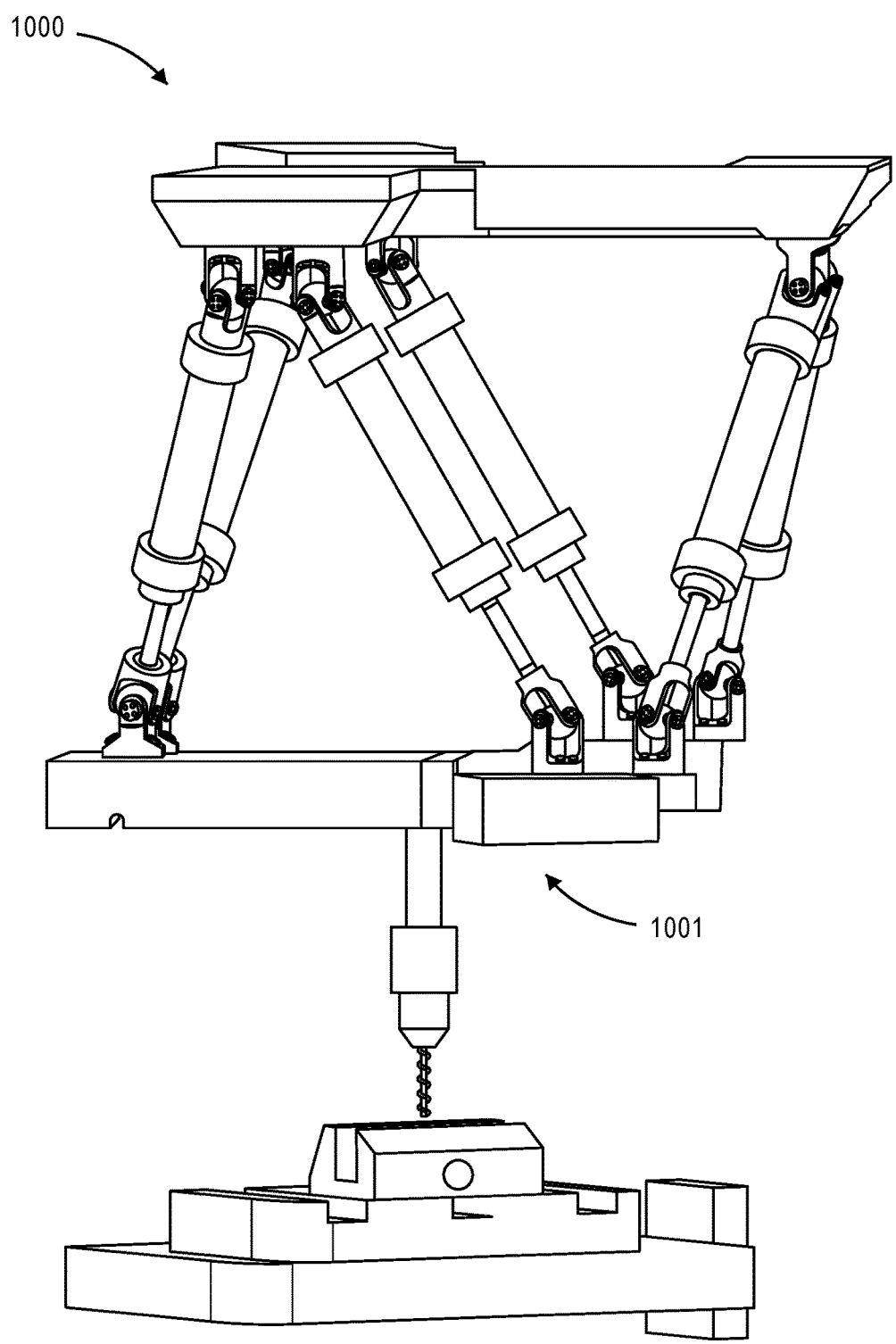
FIGS. 10A-10B are illustrations of exemplary robots that include a parallel mechanism. The parallel mechanism may be a hexapod, Stewart, Delta or any other parallel mechanisms that provides sufficient degrees of freedom (DOF) for resizing all dimensions of the pre-fabricated custom implant. A mechanical cutting tool or a laser cutter can be used with this robot.
Figure 10B:
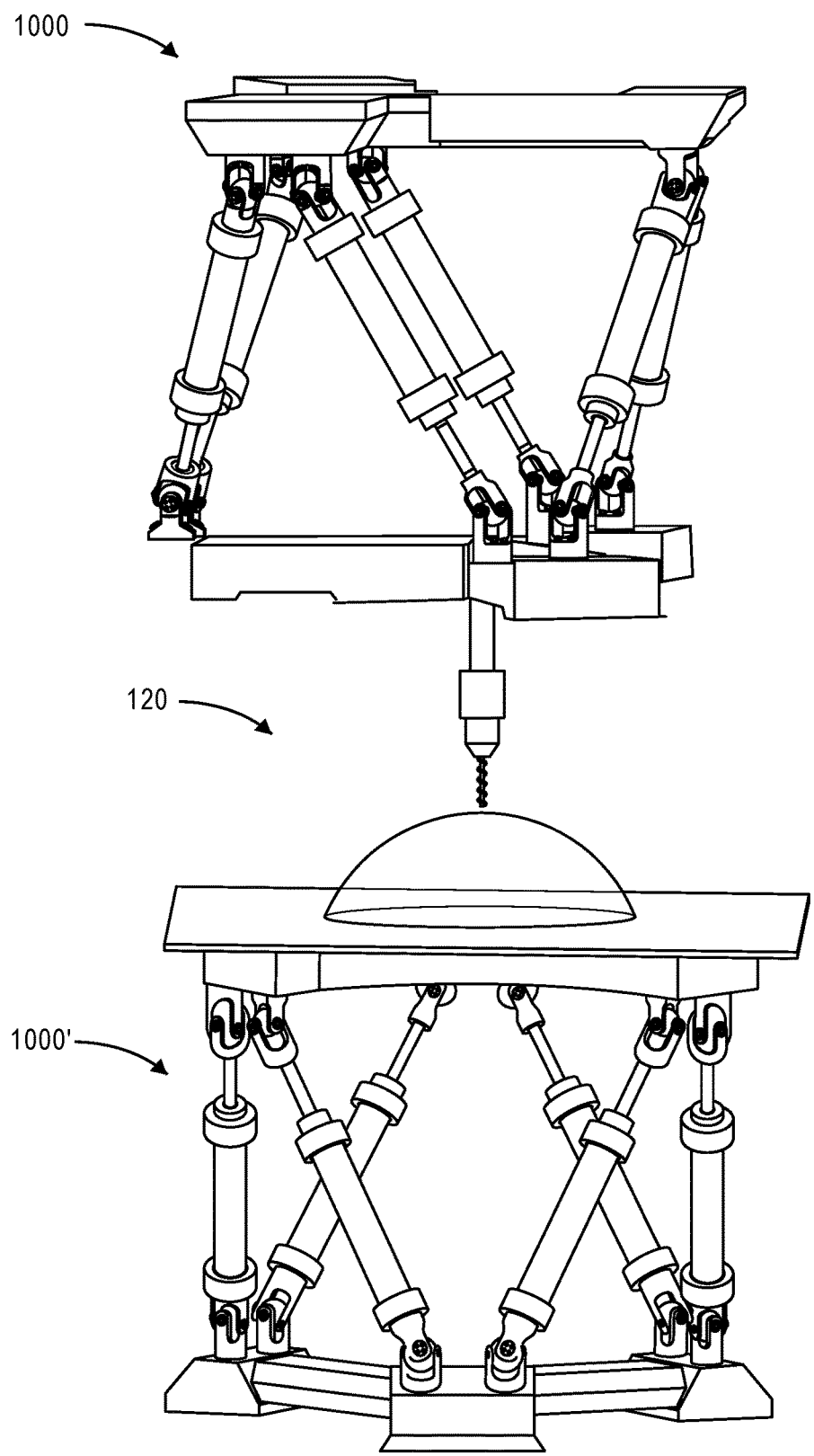
Figure 10C:
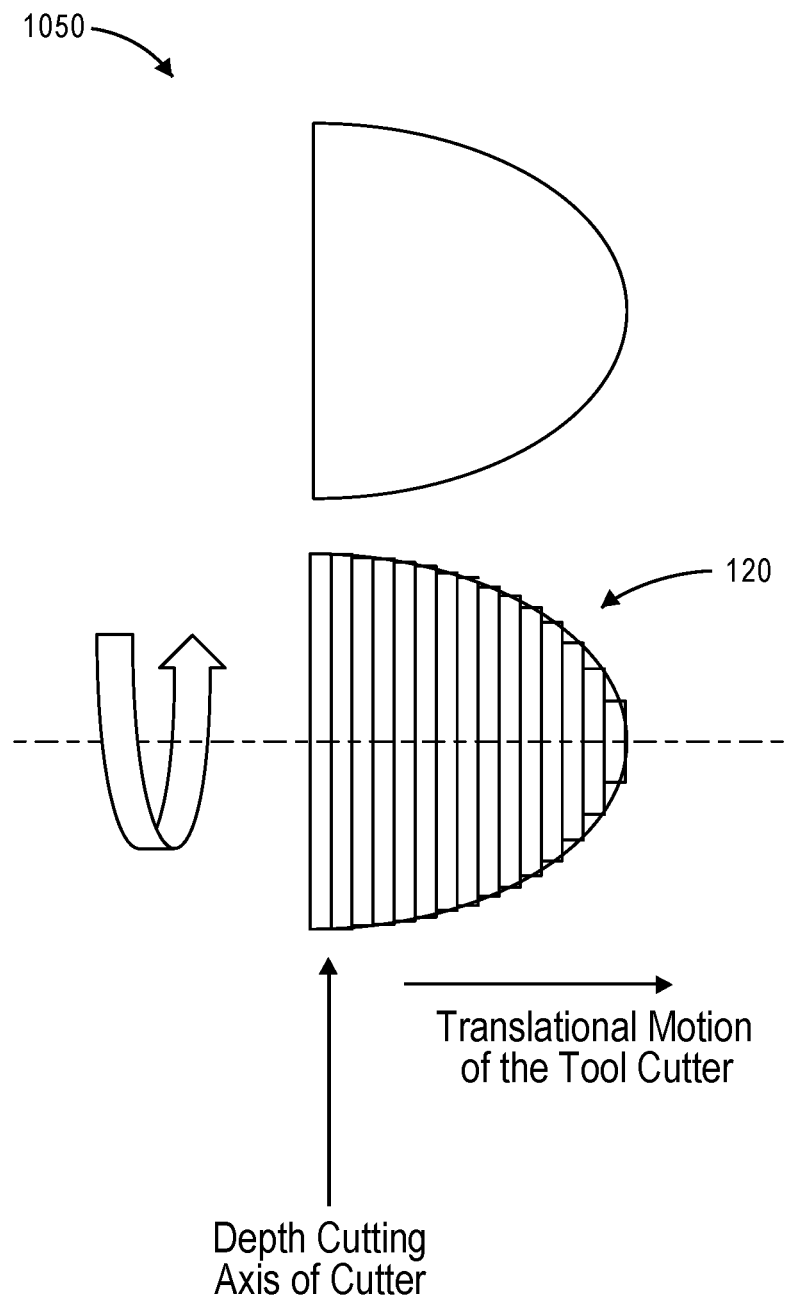
FIG. 10C is a representative implant forming scheme used by a cutting machine (CM) with respect to a rotating implant. The CM cuts the edges of the implant layer by layer. Instead of using a 6 DOF robot and an additional DOF for cutter, the proposed CM in this embodiment uses a stationary cutting tool. The implant will be attached to a rotating axis. Three additional DOF will be used to position the cutting device with respect to the implant.

Alternatively, the manufacturing device 116 may be a parallel robot 1000 such as that shown in FIG. 10A and FIG. 10B. The parallel robot 1000 in FIG. 10B may also work in cooperation with a parallel mechanism 1000' that may be a hexapod, Stewart, Delta or any other parallel mechanisms that provides sufficient degrees of freedom (DOF) for resizing the implant 120, for example, a nonstationary platform that is configured to advance or retract the implant material-removal tool toward or away from the holding platform. A cutter 1001, such as a mechanical cutting tool or a laser cutter can be used with this robotic manufacturing device.

In another embodiment, the manufacturing device, may be a subtractive manufacturing mechanism 1050 as shown in FIG. 11. Here the manufacturing device is a cutting machine that cuts the edges of the implant layer by layer. Instead of using a 6 DOF robot and an additional DOF for the cutter, the subtractive manufacturing mechanism 1050 in this embodiment uses a stationary cutting tool. The implant may be attached to a rotating axis. Three additional DOF may be used to position the cutting device with respect to the implant 120.

In yet another embodiment, the implant may be fabricated via the use of a computer-controlled tool or a tool attached to a haptic device (not shown). For the computer-controlled tool, the robot is programmed to accurately follow the path using available feedback (e.g., encoders combined with forward kinematics, or other external tracking mechanisms). When using a haptic device, virtual constraints are applied visually or via the haptic device to help a user, such as the reconstructive surgeon, to maintain the orientation of the cutter while manually reshaping the implant. In other words, an implant may be resized by removing, for example, via cutting, excess portions of an oversized implant. In reshaping an implant, cuts may be controlled through either physical information (e.g., projection of a trace line onto the implant, which is the least reliable), by some virtual constraints (e.g., not allowing the robot to move in certain positions), or both.

In yet even another embodiment, the implant may be fabricated via the use of a parallel robot (e.g., hexapod, stewart, Delta robot or any other parallel mechanisms), that may include the mechanism of FIGS. 10A-10B or a robotic arm of FIG. 9. In an example, the robot holds, moves and rotates the implant to a desired position and orientation. The cutting tool position may be fixed and may only rotate along its axis utilizing a simple motor.

Figure 11A:
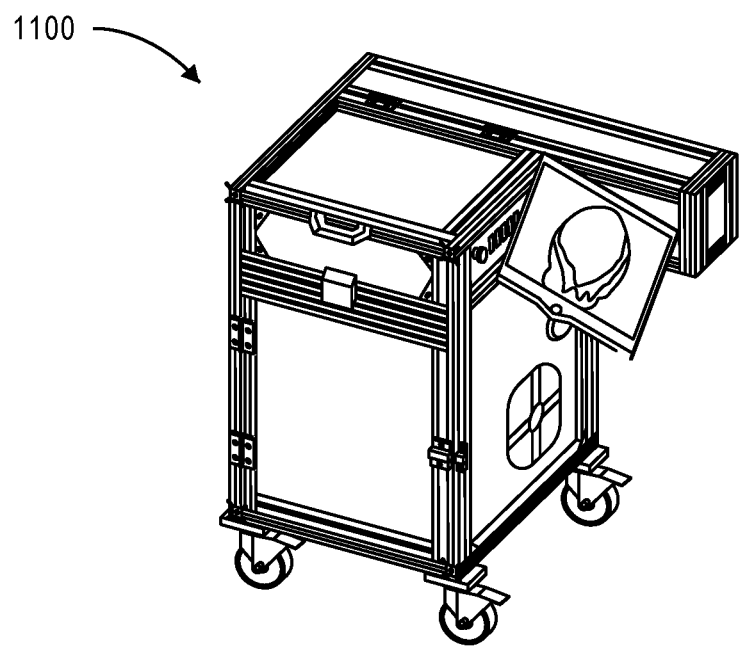
FIGS. 11A-11D are illustrations of a five-axis laser cutting machine for CCI reshaping with FIG. 11A showing an overall system view, FIG. 11B showing a CAD model of the system of FIG. 11A, FIG. 11C showing a close-up view of translational stages used for forming the CCI, and FIG. 11D showing a two-axis rotary stage used for orienting the CCI during the forming thereof.
Figure 11B:
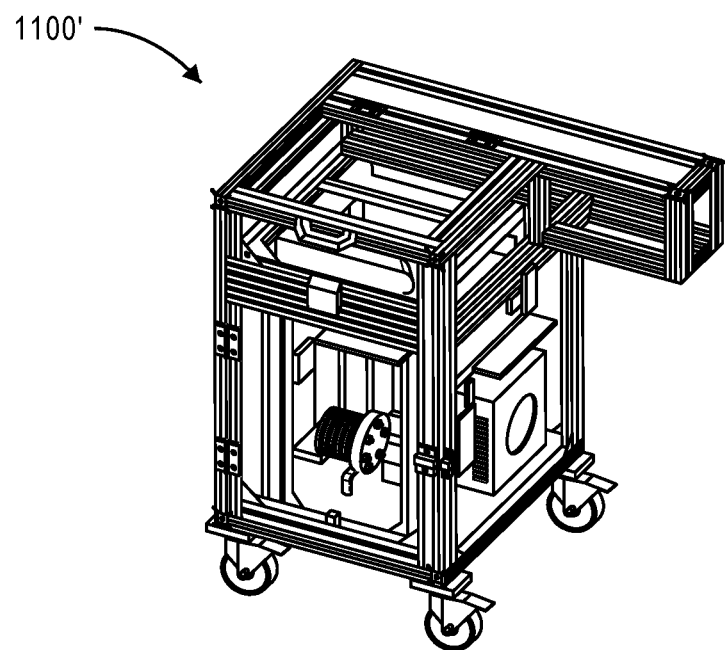
Figure 11C:
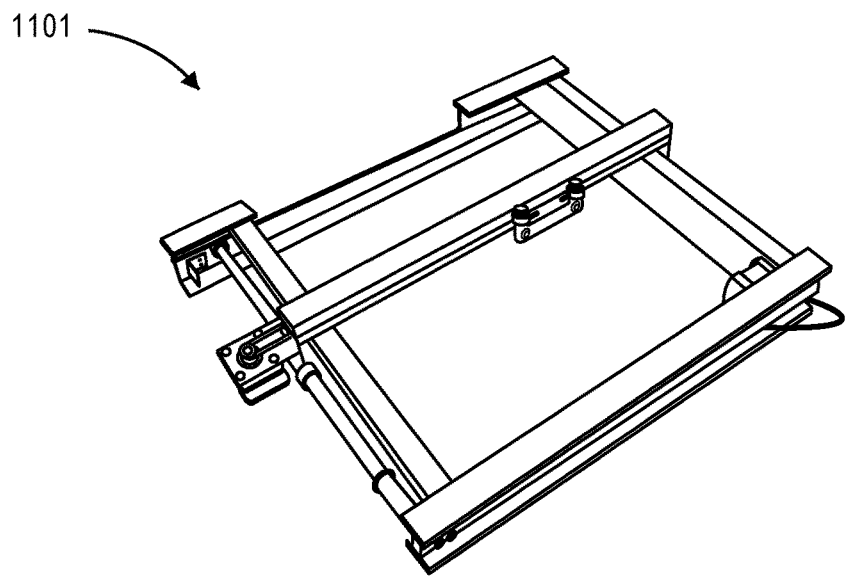
Figure 11D:
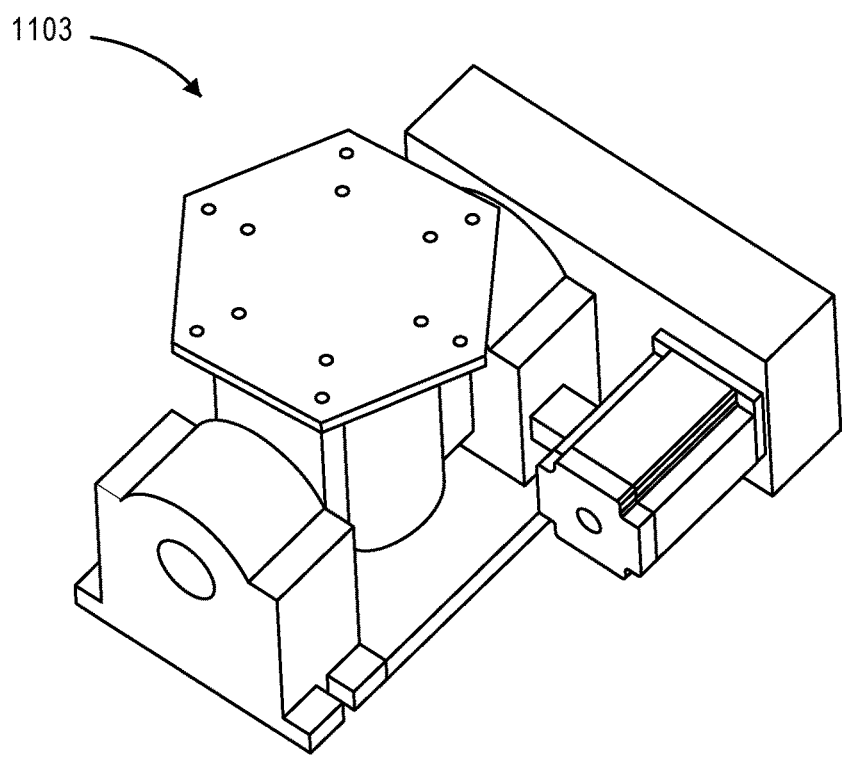
Figure 12:
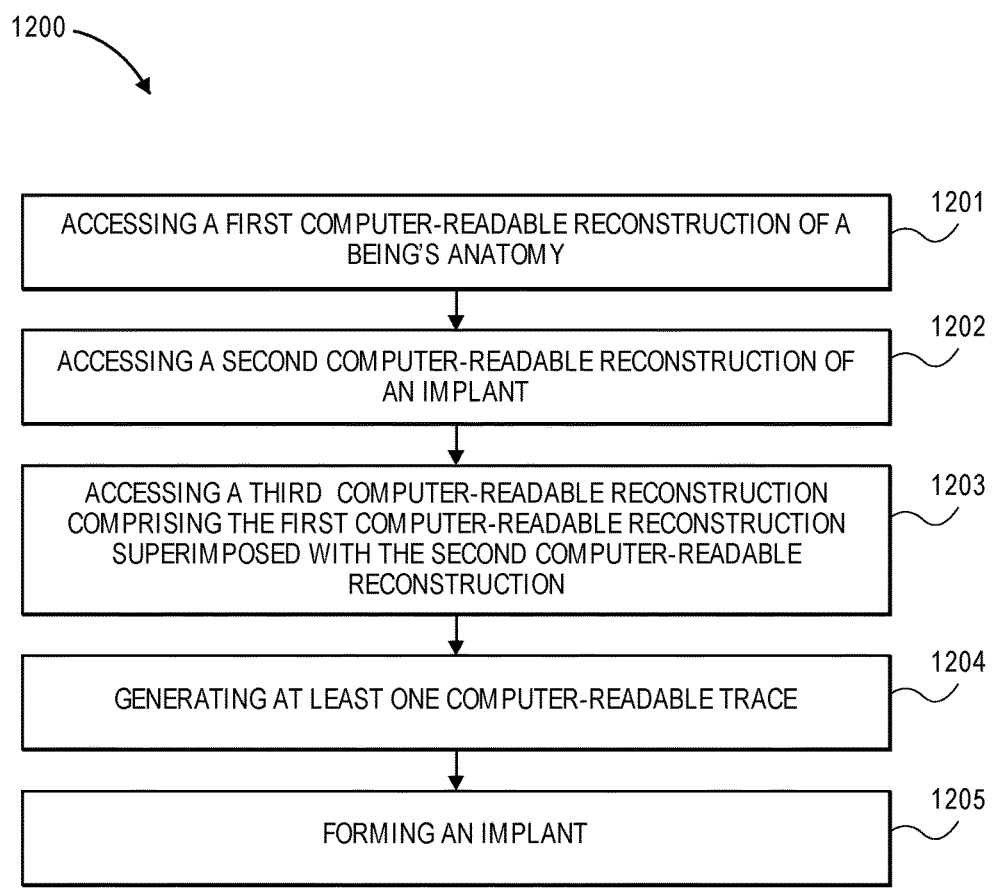
FIG. 12 is a flowchart depicting representative steps for executing a method of an embodiment.
Figure 13:
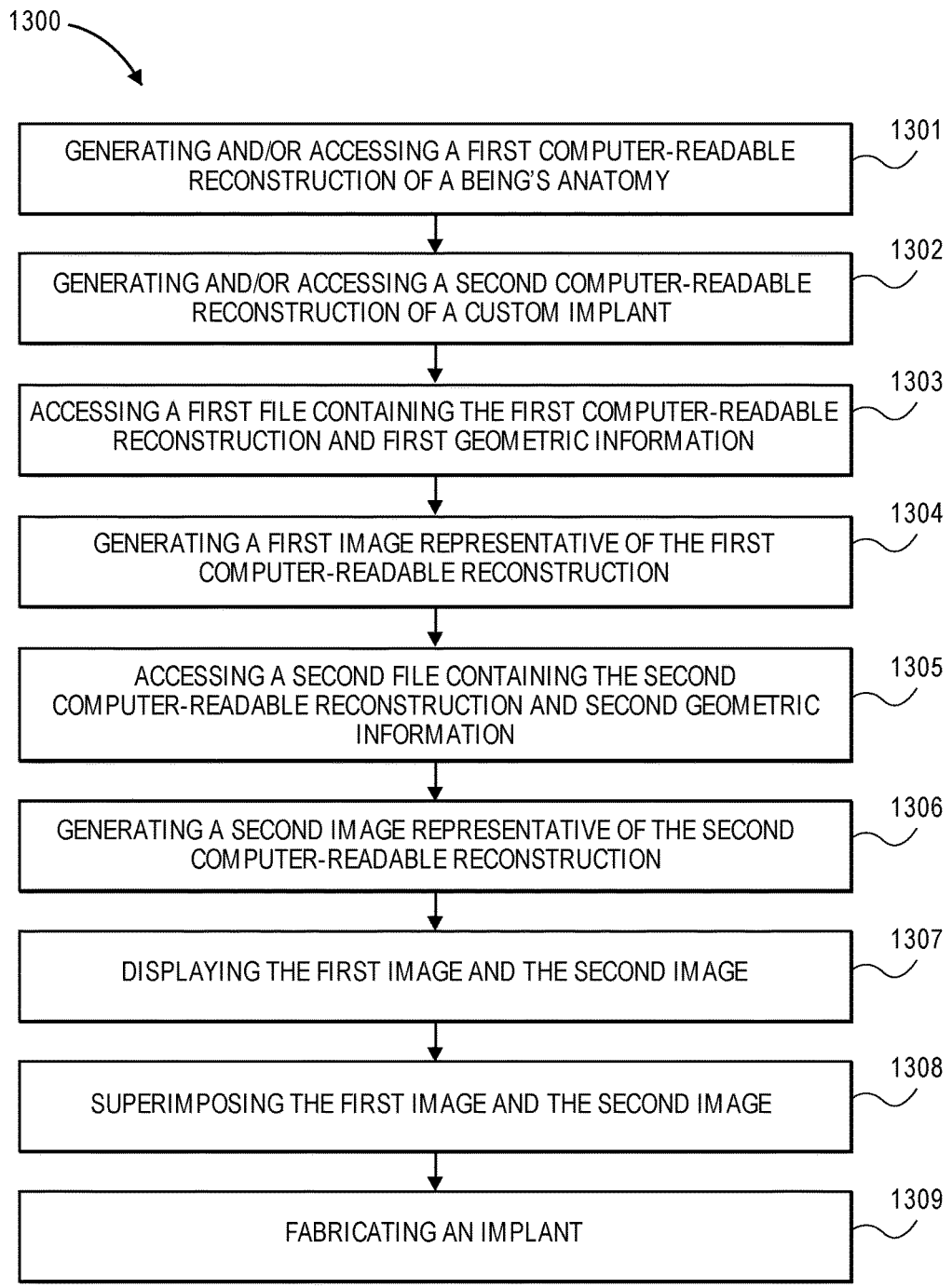
FIG. 13 is a flowchart depicting representative steps for executing a method of an embodiment.
Figure 14:
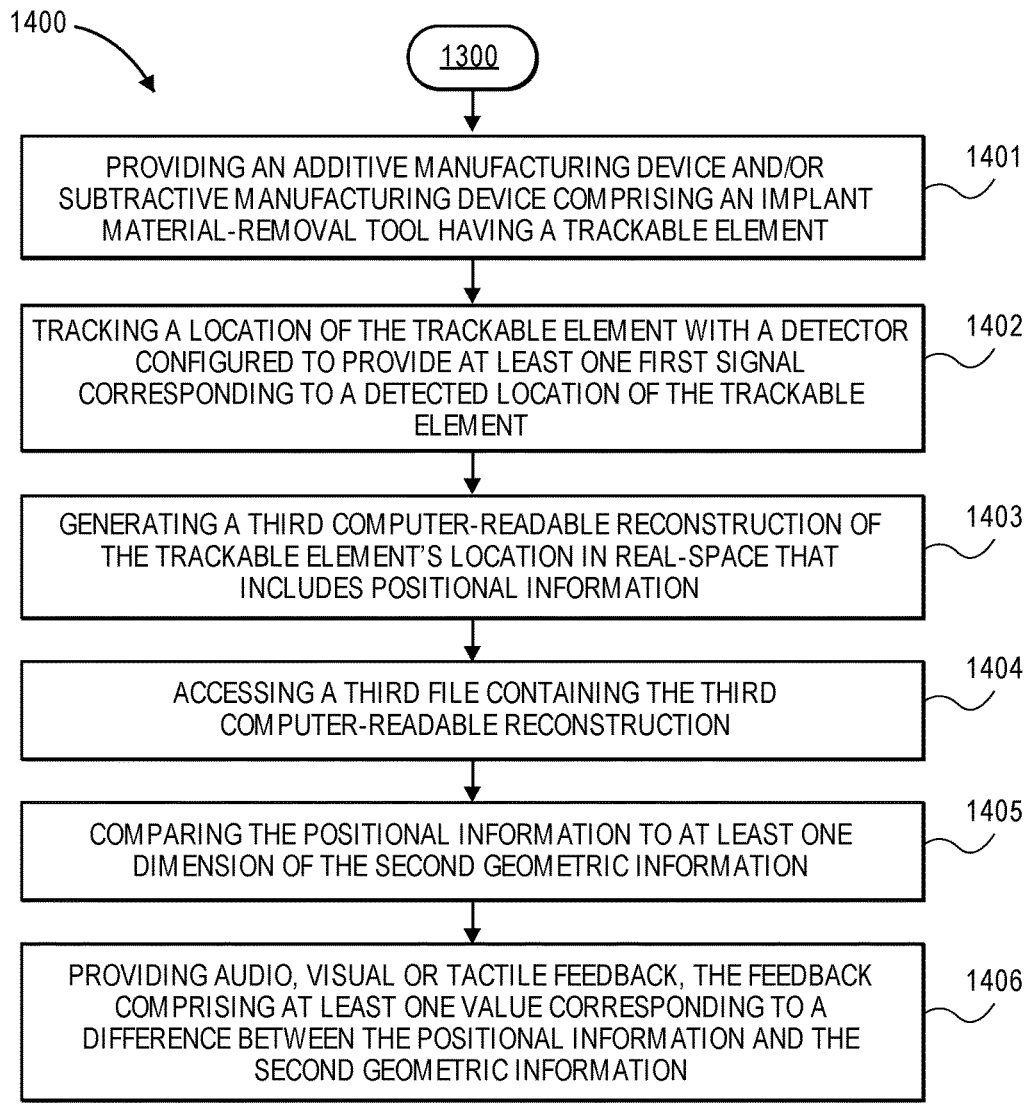
FIG. 14 is a flowchart depicting representative steps for executing a method of an embodiment.
Figure 15:
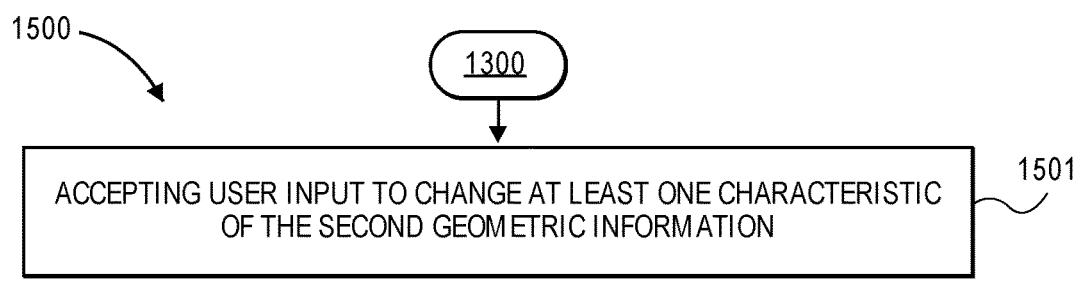
FIG. 15 is a flowchart depicting representative steps for executing a method of an embodiment.

In yet another embodiment, the implant may be fabricated via the use of a robot-assisted laser cutting system, such as a five-axis laser cutting machine 1100 shown in FIG. 11A (a CAD model 1100' of the five-axis layer cutting machine 1100 is shown in FIG. 11B). That is, a laser cutter may be used to shape the CCI while it is attached to a multi-axis robotic system. FIG. 11A depict an example five axis laser cutter machine 1100 for CCI trimming. This example of robot-assisted laser system can provide 5 axis of simultaneous motion to trim the edges of the CCI with any desired angle. An example design may include translational stages 1101 such as a three cartesian linear stage (XYZ, as shown in FIG. 11C) and a rotary table 1103 such as a two axis rotary stage used for orienting an implant (as shown in FIG. 11D).

Returning to the system 100 depicted in FIGS. 1A-1H and FIG. 6, while not particularly limited, the at least one computer 115-R may be a desktop computer, a network computer, a mainframe, a server, a handheld computer or a laptop. The at least one computer 115-R may be configured to access at least one computer readable reconstruction of at least one object, such as a being's anatomy, or at least portions of the being's anatomy, for example, a first computer readable reconstruction, a second computer readable reconstruction, and a third computer readable reconstruction. At least one of the first, second and third computer readable reconstructions may include three-dimensional (3D) views, such as those created by scanning an object, such as an implant or a patient via, for example, CT scan. At least one display may be connected to the at least one computer. The display may be configured to display a visual representation of the first, second and/or third computer readable reconstruction(s) in a format visible to a human being. The first computer may include at least one memory to store data and instructions, and at least one processor configured to access the at least one memory and to execute instructions, such as any or all of the instructions 1200, 1300, 1400, and 1500 corresponding to steps shown in the flow charts of FIGS. 12-15, respectively.

Instructions 1600 may include one or more of the steps included in the flowchart on FIG. 6. For purposes of providing examples, some of the steps are described below with reference to components shown in the views of FIGS. 1A-1C and/or system views of FIGS. 2A-2F.

In an embodiment, first instructions 1600 include accessing a first computer-readable reconstruction of a being's anatomy at 1601 and accessing a second computer-readable reconstruction of an implant at 1602. In an example, the first computer-readable reconstruction of the being's anatomy may be based on information contained in a file created by scanning the patient, such as via CT scan, and/or the second computer-readable reconstruction of the implant may be based on information contained in a file created by scanning a prefabricated implant (such as an oversized CCI) or information contained in a file created by designing an implant such as in a computer automate design (CAD) file. At 1603, the instructions may also include accessing a third computer-readable reconstruction comprising the first computer-readable reconstruction superimposed with the second computer-readable reconstruction. In an example, step 1603 may be initiated by at least one signal generated by user input, for example, via user interaction with the computer, or by a signal generated as part of a computer software program.

The instructions 1600 may also include generating at least one computer-readable trace at 1604.

In an embodiment for generating the at least one computer-readable trace, a clinician (for example, a surgeon) may acquire a point cloud from the removed anatomical feature, such as a cut region from which an anatomical specimen with disease or deformity exists (i.e., bone, soft tissue) is removed, and the anatomical defect is assessed in real-time using the CAS system as compared to its surrounding, unaltered anatomy. Digitization can be achieved through tracking technology such as an optical (infrared) tracker, or an electromagnetic tracker. A trackable pointer tool with a digitizer can be used for tracking by an optical/electromagnetic sensor (such as the sensor in FIG. 2A), and subsequently for digitizing the region of interest as, for example, a trace. However, such an embodiment is not limited to use of an optical/magnetic tracker or even manual digitization where a user manipulates such a pointer tool with a digitizer. For example, a robotic tool may be utilized as a digitizer (rather than an optical/magnetic tracker).

By using a registration between the patient anatomy and patient model, the points from the digitized trace can be transformed to a patient model. Thus, for the embodiments described herein, a method can include attaching a reference unit having a first trackable element to a first anatomical feature of a being's anatomy; detecting a location of at least the first trackable element with a detector configured to provide at least one first signal corresponding to a detected location of at least the first trackable element; accessing a first computer-readable reconstruction of the being's anatomy, the first computer-readable reconstruction comprising a first updatable orientation, wherein the first updatable orientation is updated in response to the at least one first signal; and accessing a second computer-readable reconstruction of an implant, the second computer-readable reconstruction comprising a second updatable orientation. The method also includes detecting a location of at least one second trackable element with the detector. The detector may further be configured to provide at least one second signal corresponding to a detected location of at least the second trackable element. The method also includes generating at least one updatable, computer-readable trace, wherein the trace corresponds to an updated location of the at least one second trackable element, and superimposing the least one updatable, computer-readable trace over portions of the second computer-readable reconstruction of the implant.

In another embodiment for generating a trace, camera images, with or without the use of a depth/structured light sensor, may be used to generate a 3D point cloud from which cuts are identified.

Additional steps may include controlling a subtractive or additive manufacturing device at 1605 to form an implant. In an example, the second computer-readable reconstruction of the implant generated at 1602 may include a geometry defined by at least one of: i) a shape of a resected portion of the being's anatomy represented by first geometric information corresponding to a resected portion in the first computer-readable reconstruction, and ii) a selected portion of the first computer-readable reconstruction, the selected portion comprising an anatomical feature of the being's anatomy, including but not limited to oncological defect sites, such as a benign/malignant skull neoplasm, large defects following stroke, trauma, aneurysmal bleeding, bone flap removal for infection, and oncological ablation. Additionally, the implant fabricated by the manufacturing device at 1605 may have dimensions defined by the geometry of the at least one computer-readable trace generated in step 1604.

In an embodiment, the second-readable reconstruction of the implant and/or the computer-readable trace may be generated via a system that utilizes a depth or structured light sensor. Generally, a computer-assisted surgical method can include the following: a) create a representative 3D point cloud of the patient from signals generated by a 3D sensor; b) register the 3D point cloud to a preoperative CT model of the patient; c) identify bone cuts (such as a resected area of the patient's anatomy) using either 3D point cloud information, RGB camera information, or a combination thereof to generate cut information (such as cut geometry information); d) provide the cut information, to a robot/cutting machine; e) the robot automatically resizes/reshapes the implant; and f) the implant is attached to the patient.

In an embodiment a computer-assisted surgical method includes use of the CAS system, which may provide a user an enhanced implant reconstruction experience, for example, providing a surgeon unprecedented, immediate visual feedback and allowing single-stage implant cranioplasty and all related craniomaxillofacial reconstruction for scenarios related to skull neoplasms, etc—in situations where the tumor defect is not known beforehand, but where a customized implant is needed requiring on-table modification via CAS system guidance. Generally, the method can include the following: a) generating and/or accessing a computer-readable reconstruction of a patient's anatomy, such as via a preoperative CT scan that includes an anatomical feature, such as a defect, and constructing a 3D model of the anatomy; b) preselecting a resection area on the model; c) determining implant dimensions (can be a few centimeters (cms) greater along the periphery than the size of the anticipated defect) and fabricate the implant with an additive and/or subtractive manufacturing device; d) attaching a reference unit having a trackable element onto the patient's anatomy, such as at the patient's skull; e) registering the location of the trackable element/reference unit to the computer-readable reconstruction (preoperative CT scan); f) using a detector to generate a signal in response to forming a trace of the defect boundaries, for example, if additional resection is required; g) superimposing information corresponding to signals generated by optical digitizer, such as signals in response to forming a trace of the defect boundaries, on the computer-readable reconstruction; h) forming an implant according to a geometry corresponding to the trace; i) tracking the custom implant with respect to preoperative plan and recipient's unaltered anatomy, j) attaching the implant to the patient; and k) obtaining a postoperative image of the patient and the attached implant, such as a CT scan.

In another embodiment, a virtual representation of the oversized implant (i.e., a computer-readable representation of the oversized implant) can be generated and accessed by the CAS system. A surgeon may then use a marking tool (e.g., sterile marking pen) to outline the projected points (the trace from the anatomy). The robot then cuts along the outline of the projected points and fits the implant into exact place in a less time-intense, labor-intense manner. Significant time reduction (by up to 90%) and improved implant-to-defect positioning (i.e., less gap space between implant and surrounding bone) are both significant advantages of this invention.

The method may include any step or combination of steps included in the flow charts of FIG. 6-9 and described below. In an example shown in the flow-chart of FIG. 7, a method 1700 can include generating and/or accessing a first computer-readable reconstruction of a being's anatomy at 1701. The method may also include generating and/or accessing a second computer-readable reconstruction of a custom implant at 1702. The method may also include accessing a first file containing the first computer-readable reconstruction and first geometric information at 1703 and generating a first image representative of the first computer-readable reconstruction at 1704. The method may also include accessing a second file containing the second computer-readable reconstruction and second geometric information at 1705 and generating a second image representative of the second computer-readable reconstruction at 1706. The method 1700 may further include displaying the first image and the second image at 1707, and superimposing the first image and the second image at 1708. The method may further include fabricating an implant at 1709, which may be accomplished with an R/CM that receives signals representative of the dimensions required for the implant.

In an example, an anatomical discrepancy between the anatomical feature of interest (such as a resected portion of the being's anatomy) and the fabricated implant may be minimized based on a preselected tolerance, for example, in instructions provided for fabricating the implant, including instructions provided in computer-readable files, such as digital data, provided to an implant manufacturing device. The methods described herein may also include attaching the implant to the preselected anatomical feature of interest, such as to a patients anatomy surrounding oncological defect sites, such as a benign/malignant skeletal neoplasm, or large defect sites formed following stroke, trauma, aneurysmal bleeding, bone flap removal for osteomyelitic infection, or oncological ablation, as depicted, for example in FIG. 1C. After using the CAS for guidance, the implantation of the implant, for example, the methods of the embodiments can also include obtaining a post operative image of at least the implant attached to the preselected anatomical feature. For example, a CT scan may be taken of the patient with implant attached.

In an embodiment, a method 1800 depicted by the flowchart in FIG. 8 may include all or some of the steps 1700 of FIG. 7 and may also include any step or combination of steps included in the flow charts of FIG. 6 and FIG. 9. In an example shown in the flow chart of FIG. 8, in addition to some or all the steps of method 1700, method 1800 may include providing an additive and/or subtractive manufacturing device. The subtractive manufacturing device may include an implant material-removal tool which may have a trackable element. The trackable element may not be limited to any external trackable element, the position of which is sensed by a sensor, but may include embedded encoders that identify the motor position. Embedded encoders in, for example, a robot/cutting machine more accurately provide positional information and can be used to ensure that the robot/cutting machine is following the correct path to resize/reshape an implant. The method may also include tracking a location of the trackable element with a detector at 1802. The detector may be configured to provide at least one first signal corresponding to a detected location of the trackable element. At 1803, the method may also include generating and/or accessing a third computer-readable reconstruction of the trackable element's location in real-space. The computer-readable reconstruction may include positional information, such as information providing a position of the trackable element relative to a sensed location sensed by the detector. The method may also include accessing a third file containing the third computer-readable reconstruction at 1804. The method can further include comparing the positional information to at least one dimension of the second geometric information at 1805. The method can further include providing audio, visual or tactile feedback, the feedback comprising at least one value corresponding to a difference between the positional information and the second geometric information at 1806. For example, to provide an end user with feedback, such as to assist a user manually operating a cutting tool to more accurately remove excess material from an oversized CCI, a comparison can be made between a location of the cutting tool relative to geometric information of the generated second computer-readable reconstruction of a custom implant. As such, if the end user moves the cutter to a location on the actual oversized implant for which should not be removed, the end user may receive indication that such movement is not optimal.

Finally, in an embodiment, a method 1900 depicted by the flowchart in FIG. 9 may include all or some of the steps 1700 of FIG. 7 and may also include any step or combination of steps included in the flow charts of FIGS. 6 and 8. The method may also include tracking and accepting user input to change at least one characteristic of the second geometric information.

The described methods of the embodiments may be utilized during a surgical procedure, such as a surgical implantation procedure for various forms of craniomaxillofacial surgery and/or neurosurgery including an implant-based cranioplasty. Accordingly, the implant may be a custom, 3D craniofacial implant made of either alloplastic materials or biologic tissue engineered cells as described above and a being, such as a recipient being, on whom the surgical procedure is performed.

As used herein, to the extent that the terms "coupled," "connected," and "connecting", or variants thereof are used in either the detailed description and the claims, such terms are intended to refer to "in direct connection with" or "in connection with via one or more intermediate elements or members." Furthermore, to the extent that the terms "including", "includes", "having", "has", "with", or variants thereof are used in either the detailed description and the claims, such terms are intended to be inclusive in a manner similar to the term "comprising." As used herein, the phrase "at least one of" or "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for forming an implant with an autonomous manufacturing device, comprising:
    accessing a first computer-readable reconstruction of a being's anatomy;
    forming an implant corresponding to a portion of the being's anatomy, the implant comprising a polymer, a metal, a bioengineered material, or a combination thereof;
    accessing a second computer-readable reconstruction of the implant;
    resecting a portion of the being's anatomy creating a boundary defect defining the resected portion of the being's anatomy;
    generating at least one computer-readable trace from a point cloud of the boundary defect of the being's anatomy with an anatomical feature removed; and
    removing excess material from a periphery of the implant to form the implant into a shape defined by the computer-readable trace.

2. The method of claim 1, wherein the step of removing includes causing an implant material-removal tool of an autonomous manufacturing device to remove the excess material from the implant.

3. The method of claim 2, further comprising generating a projected trace from the computer-readable trace, wherein the projected trace comprises a 2D or 3D projected trace, and projecting the projected trace onto the implant.

4. The method of claim 3, further including the step of accessing a third computer-readable reconstruction comprising the first computer-readable reconstruction superimposed with the second computer readable reconstruction.

5. The method of claim 1, wherein the computer-readable trace includes information for generating signals to virtually constrain a human-guided cutting tool using an autonomous manufacturing device.

6. The method of claim 5, wherein the human-guided cutting tool using the autonomous manufacturing device is configured to provide haptic feedback.

7. The method of claim 1, wherein the step of removing includes removing portions of the implant that are adjacent to a boundary defined by at least one dimension of the computer-readable trace.

8. The method of claim 1, further comprising fitting the implant onto the being.

9. The method of claim 1, wherein the wherein the step of forming is performed by an autonomous manufacturing device.

10. The method of claim 9, wherein the step of removing is performed by the autonomous manufacturing device.

11. The method of claim 10, wherein the autonomous manufacturing device comprises an articulating arm and an implant material-removal tool detachably connected to an end of the articulating arm.

12. The method of claim 10, wherein the autonomous manufacturing device comprises an implant material-removal tool disposed on a nonstationary platform and a holding platform on which implant material is attached, wherein the nonstationary platform is configured to advance or retract the implant material-removal tool toward or away from the holding platform.

13. The method of claim 12, wherein the implant material-removal tool comprises a cutting surface for cutting the implant material.

14. The method of claim 12, wherein the implant material-removal tool comprises a laser for ablating the implant material.

15. The method of claim 12, wherein the holding platform comprises a nonstationary platform.

16. The method of claim 12, wherein the holding platform comprises a stationary platform.

17. The method of claim 1, wherein the step of removing is performed by an autonomous manufacturing device comprising an implant material-removal tool.

18. The method of claim 17, wherein the computer-readable trace includes information for generating signals to virtually constrain a human-guided cutting tool using the autonomous manufacturing device with the use of at least one of motor encoders, a position trackable element and/or an electromagnetic trackable element.

19. The method of claim 18, wherein the human-guided cutting tool comprises a haptic device, wherein the haptic device receives signals generated in response to the signals generated by the at least one of motor encoders, a position trackable element and/or an electromagnetic trackable element in order to generate a haptic response provided by the human-guided cutting tool.

20. The method of claim 1, the computer-readable trace comprises a virtual or visual representation of a geometry corresponding to a final shape of a resized implant.

21. The method of claim 1, wherein the implant is formed with a curvature specific to that of the being's anatomy.

22. The method of claim 1, wherein the step of removing is performed by an autonomous manufacturing device comprising a multi-axis laser cutter machine.

* * * * *